(12) United States Patent
Macoviak et al.

(10) Patent No.: US 6,361,545 B1
(45) Date of Patent: *Mar. 26, 2002

(54) PERFUSION FILTER CATHETER

(75) Inventors: John A. Macoviak, La Jolla; James J. Leary, Sunnyvale; Wilfred J. Samson, Saratoga, all of CA (US)

(73) Assignee: Cardeon Corporation, Cupertino, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/158,405

(22) Filed: Sep. 22, 1998

Related U.S. Application Data

(60) Provisional application No. 60/060,117, filed on Sep. 26, 1997.

(51) Int. Cl.$^7$ .............................................. A61M 29/00
(52) U.S. Cl. ........................ 606/200; 606/151; 606/194
(58) Field of Search ................................ 606/191, 192, 606/194, 198, 200, 113, 151, 114; 604/265

(56) References Cited

U.S. PATENT DOCUMENTS

| 3,996,938 A | 12/1976 | Clark, III |
| 4,494,531 A | 1/1985 | Gianturco |

(List continued on next page.)

FOREIGN PATENT DOCUMENTS

| EP | 86201487.5 | 8/1986 |
| WO | WO 97/17100 | 5/1997 |
| WO | WO 97/42879 | 11/1997 |
| WO | WO 98/02084 | 1/1998 |
| WO | WO 98/24377 | 6/1998 |

OTHER PUBLICATIONS

Technical Specifications Percluder® aortic occluding balloon, Datascope Corp. © 1987 Datascope Corp.

(List continued on next page.)

*Primary Examiner*—David O. Reip
*Assistant Examiner*—Julian W. Woo
(74) *Attorney, Agent, or Firm*—Fulwider Patton Lee & Utecht

(57) ABSTRACT

A perfusion filter catheter is used to capture potential emboli within the aorta during heart surgery and cardiopulmonary bypass. An expandable embolic filter assembly having fine filter mesh for capturing macroemboli and microemboli is mounted on a catheter shaft having a perfusion lumen with perfusion ports located upstream of the filter. The embolic filter assembly can be actively or passively deployed within the ascending aortic. An optional outer tube covers the embolic filter assembly to prevent premature deployment. Radiopaque markers, sonoreflective markers and/or an aortic transillumination system are provided to monitor the position of the catheter and the deployment state of the embolic filter assembly. The embolic filter assembly is configured to maximize the effective filter surface area when deployed. Embolic filter assembly configurations described include an elongated cone, a frustum of a cone, a trumpet-shape, a modified trumpet-shape, and helically, circumferentially and longitudinally convoluted shapes, as well as configurations having standoff members for centering the filter and holding the filter mesh away from the aortic walls when deployed. Oxygenated blood is perfused through the perfusion lumen and any embolic materials that might be dislodged are captured in the deployed embolic filter assembly. Embodiments are also described that combine the perfusion filter catheter with an aortic occlusion device, which may be a toroidal balloon, an expandable balloon or a selectively deployable external catheter flow control valve. The combined device allows percutaneous transluminal administration of cardiopulmonary bypass and cardioplegic arrest with protection from undesirable embolic events.

25 Claims, 25 Drawing Sheets

U.S. PATENT DOCUMENTS

| | | | |
|---|---|---|---|
| 4,650,466 A | 3/1987 | Luther | |
| 4,723,549 A | 2/1988 | Wholey et al. | |
| 4,793,348 A | 12/1988 | Palmaz | |
| 4,817,600 A | 4/1989 | Herms et al. | |
| 4,873,978 A | 10/1989 | Ginsburg | |
| 4,969,891 A | 11/1990 | Gewertz | 606/200 |
| 5,059,205 A | 10/1991 | El-Nounou et al. | 606/200 |
| 5,108,418 A | 4/1992 | Lefebvre | 606/200 |
| 5,108,419 A | 4/1992 | Reger et al. | 606/200 |
| 5,135,516 A * | 8/1992 | Sahatjian et al. | 604/265 |
| 5,152,777 A | 10/1992 | Goldberg et al. | 606/200 |
| 5,324,304 A | 6/1994 | Rasmussen | 606/200 |
| 5,375,612 A | 12/1994 | Cottenceau et al. | 128/899 |
| 5,415,630 A | 5/1995 | Gory | 604/53 |
| 5,496,277 A | 3/1996 | Termin et al. | 604/104 |
| 5,549,626 A | 8/1996 | Miller | 606/200 |
| 5,662,671 A | 9/1997 | Barbut et al. | 606/170 |
| 5,695,519 A * | 12/1997 | Summers et al. | 606/200 |
| 5,769,816 A | 6/1998 | Barbut et al. | 604/96 |
| 5,814,064 A * | 9/1998 | Daniel et al. | 606/200 |
| 5,846,260 A | 12/1998 | Maahs | 606/200 |
| 5,935,139 A * | 8/1999 | Bates | 606/159 |
| 6,013,093 A * | 1/2000 | Nott et al. | 606/200 |

OTHER PUBLICATIONS

Barbut et al., "Determination or Size of Aortic Emboli and Embolic Load During Coronary Artery Bypass Grafting," *Ann Thorac Surg*; 63:1262–7 (1997).

Barbut et al., "Aortic Atheromatosis and Risks of Cerebral Embolization," *J Card & Vasc Anesth*; vol. 10, No. 1,: pp 24–30 (1996).

Barbut et al., "Aortic Atheroma is Related to Outcome but not Numbers of Emboli During Coronary Bypass," *Ann Thorac Surg*; 64:454–9 (1997).

Roach et al., "Adverse Cerebral Outcomes After Coronary Artery Bypass Surgery," *N Engl J Med*, vol. 335, No. 25; pp. 1857–1863 (1996).

Aberg, "Signs of Brain Cell Injury During Open Heart Operations: Past and Present," *Ann Thorac Surg*; 59:1312–5 (1995).

Murkin, "The Role of CPB Management in Neurobehavioral Outcomes After Cardiac Surgery," *Ann Thorac Surg*; 59:1308–11 (1995).

Mills, "Risk Factors for Cerebral Injury and Cardiac Surgery," *Ann Thorac Surg* 1995, 59:1296–9.

Moody et al., "Brain Microemboli Associated with Cardiopulmonary Bypass: A Histologic and Magnetic Resonance Imaging Study," *Ann Thorac Surg*; 59:1304–7 (1995).

Murkin et al., "Statement of Consensus on Assessment of Neurobehavioral Outcomes After Cardiac Surgery," *Ann Thorac Surg*; 59:1289–95 (1995).

Sherman et al., "Heart–Brain Interactions: Neurocardiology Comes of Age," *Mayo Clin Proc*; 62:1158–1160 (1987).

van der Linden, "Cerebral Hemodynamics After Low–Flow Versus No–Flow Procedures," *Ann Thorac Surg*; 59:1321–5 (1995).

Newman et al., "Predictors of Cognitive Decline After Cardiac Operation," *Ann Thorac Surg*; 59:1326–30 (1995).

Venn et al., "Cardiopulmonary Bypass: Perioperative Cerebral Blood Flow and Postoperative Cognitive Deficit," *Ann Thorac Surg*; 59:1331–5 (1995).

Blauth, "Macroemboli and Microemboli During Cardiopulmonary Bypass," *Ann Thorac Surg*; 59:1300–3 (1995).

Sotaniemi, "Long–Term Neurologic Outcome After Cardiac Operation," *Ann Thorac Surg*; 59:1336–9 (1995).

* cited by examiner

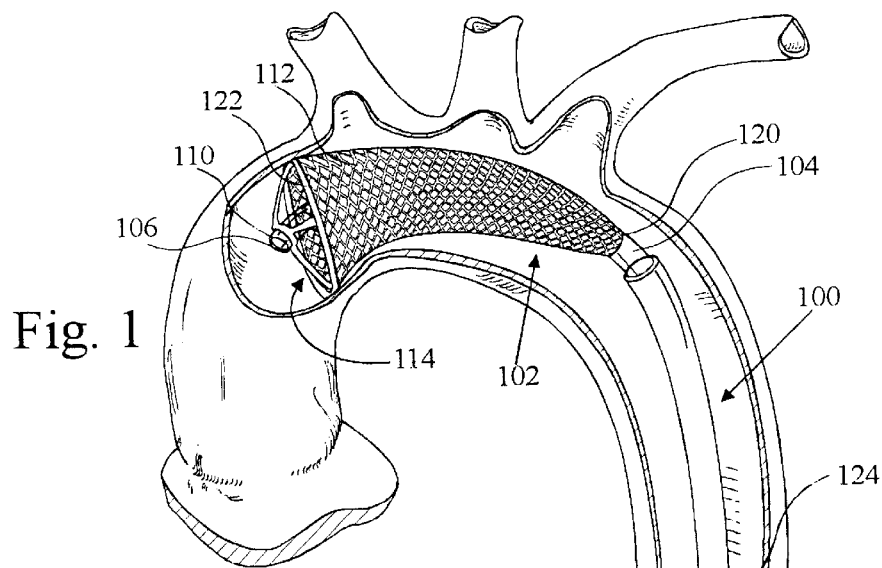
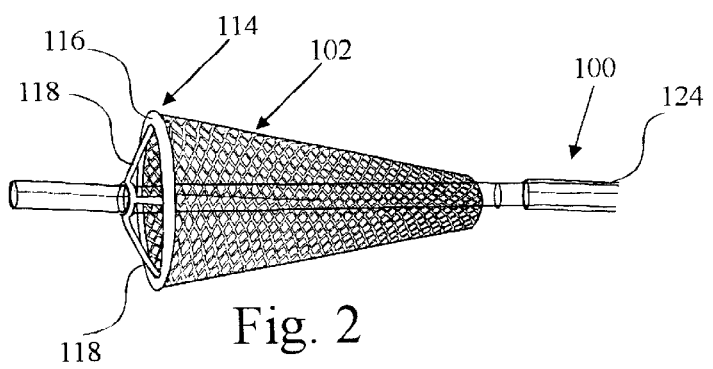
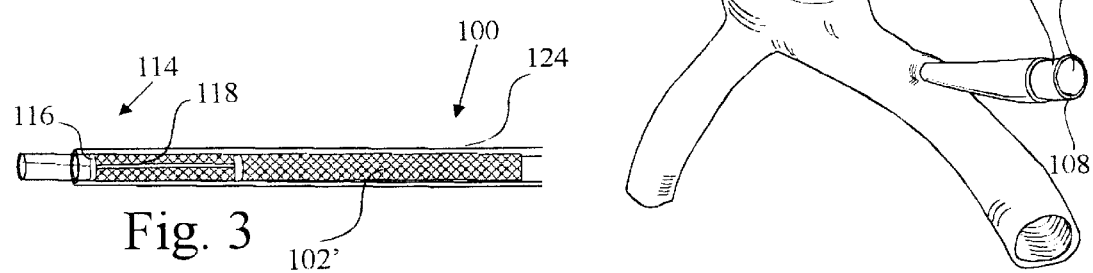

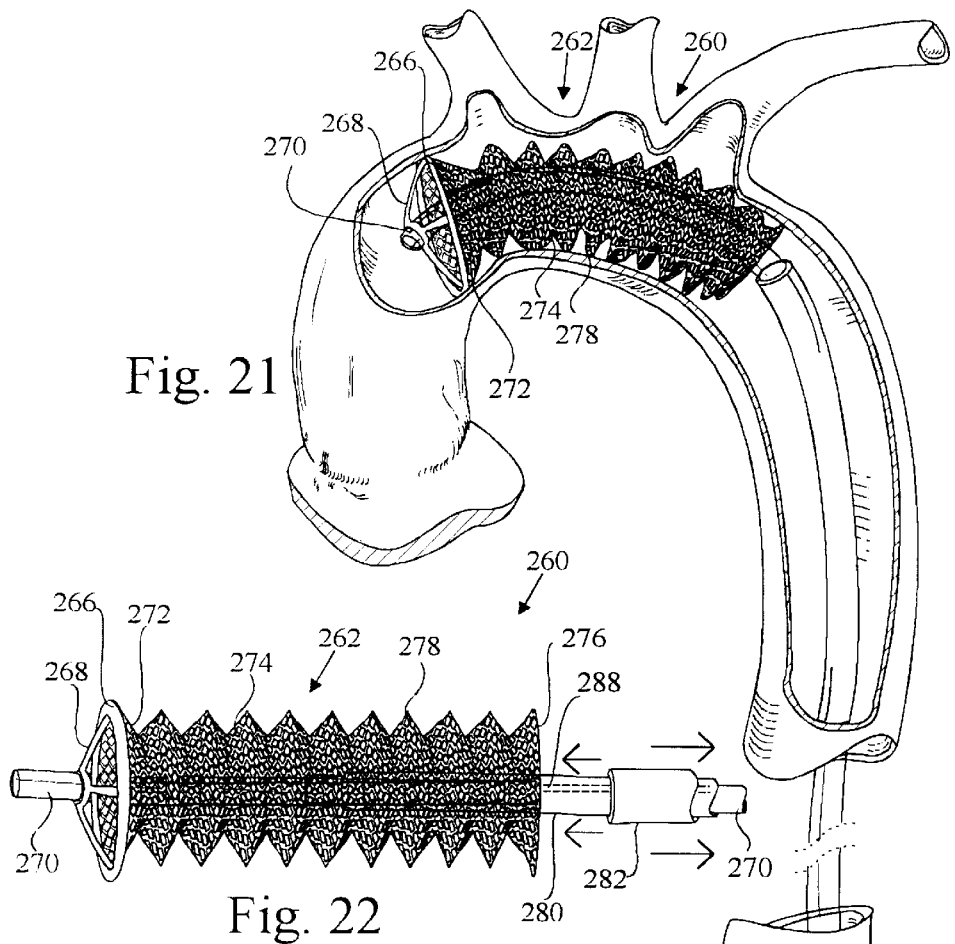
Fig. 21
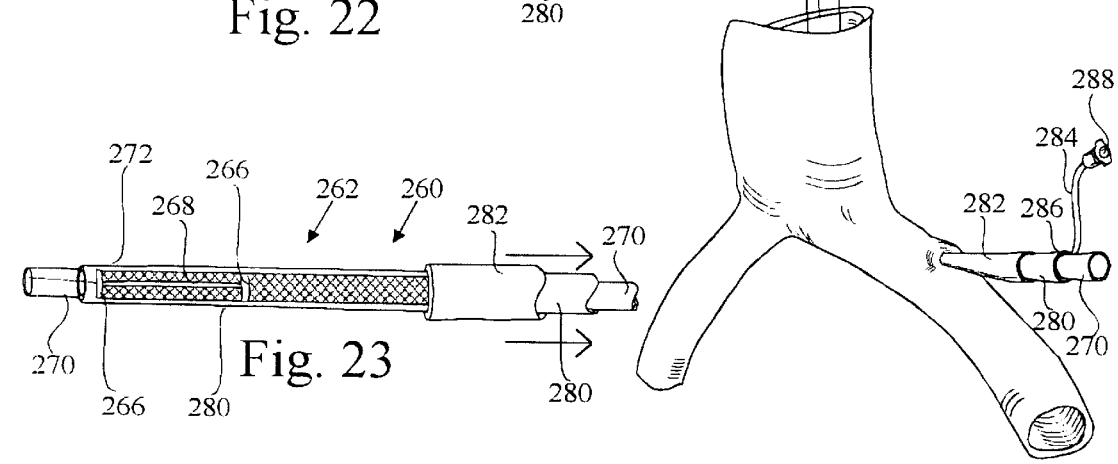
Fig. 22
Fig. 23

PERFUSION FILTER CATHETER

CROSS REFERENCE TO OTHER APPLICATIONS

This application claims the benefit of U.S. Provisional Application No. 60/060,117, filed Sep. 26, 1997, the specification of which is hereby incorporated by reference in its entirety.

FIELD OF THE INVENTION

The present invention relates generally to a catheter or cannula for infusion of oxygenated blood or other fluids into a patient for cardiopulmonary support and cerebral protection. More particularly, it relates to an arterial perfusion catheter with a deployable embolic filter for protecting a patient from adverse effects due to emboli that are dislodged during cardiopulmonary bypass.

BACKGROUND OF THE INVENTION

Over the past decades tremendous advances have been made in the area of heart surgery, including such life saving surgical procedures as coronary artery bypass grafting (CABG) and cardiac valve repair or replacement surgery. Cardiopulmonary bypass (CPB) is an important enabling technology that has helped to make these advances possible. Recently, however, there has been a growing awareness within the medical community and among the patient population of the potential sequelae or adverse affects of heart surgery and of cardiopulmonary bypass. Chief among these concerns is the potential for stroke or neurologic deficit associated with heart surgery and with cardiopulmonary bypass. One of the likely causes of stroke and of neurologic deficit is the release of emboli into the blood stream during heart surgery. Potential embolic materials include atherosclerotic plaques or calcific plaques from within the ascending aorta or cardiac valves and thrombus or clots from within the chambers of the heart. These potential emboli may be dislodged during surgical manipulation of the heart and the ascending aorta or due to high velocity jetting (sometimes called the "sandblasting effect") from the aortic perfusion cannula. Air that enters the heart chambers or the blood stream during surgery through open incisions or through the aortic perfusion cannula is another source of potential emboli. Emboli that lodge in the brain may cause a stroke or other neurologic deficit. Clinical studies have shown a correlation between the number and size of emboli passing through the carotid arteries and the frequency and severity of neurologic damage. At least one study has found that frank strokes seem to be associated with macroemboli larger than approximately 100 micrometers in size, whereas more subtle neurologic deficits seem to be associated with multiple microemboli smaller than approximately 100 micrometers in size. In order to improve the outcome of cardiac surgery and to avoid adverse neurological effects it would be very beneficial to eliminate or reduce the potential of such cerebral embolic events.

Several medical journal articles have been published relating to cerebral embolization and adverse cerebral outcomes associated with cardiac surgery, e.g.: Determination or Size of Aortic Emboli and Embolic Load During Coronary Artery Bypass Grafting; Barbut et al.; Ann Thorac Surg 1997;63;1262–7; Aortic Atheromatosis and Risks of Cerebral Embolization; Barbut et al.; J Card & Vasc Anesth, Vol 10, No 1, 1996: pp 24; Aortic Atheroma is Related to Outcome but not Numbers of Emboli During Coronary Bypass; Barbut et al.; Ann Thorac Surg 1997;64;454–9; Adverse Cerebral Outcomes After Coronary Artery Bypass Surgery; Roach et al.; New England J of Med, Vol 335, No 25, 1996: pp 1857–1863; Signs of Brain Cell Injury During Open Heart Operations: Past and Present; Aberg; Ann Thorac Surg 1995;59;1312–5; The Role of CPB Management in Neurobehavioral Outcomes After Cardiac Surgery; Murkin; Ann Thorac Surg 1995;59;1308–11; Risk Factors for Cerebral Injury and Cardiac Surgery; Mills; Ann Thorac Surg 1995;59;1296–9; Brain Microemboli Associated with Cardiopulmonary Bypass: A Histologic and Magnetic Resonance Imaging Study; Moody et al.; Ann Thorac Surg 1995;59;1304–7; CNS Dysfunction After Cardiac Surgery: Defining the Problem; Murkin; Ann Thorac Surg 1995;59;1287+Statement of Consensus on Assessment of Neurobehavioral Outcomes After Cardiac Surgery; Murkin et al.; Ann Thorac Surg 1995;59;1289–95; Heart-Brain Interactions: Neurocardiology Comes of Age; Sherman et al.; Mayo Clin Proc 62:1158–1160, 1987; Cerebral Hemodynamics After Low-Flow Versus No-Flow Procedures; van der Linden; Ann Thorac Surg 1995;59;1321–5; Predictors of Cognitive Decline After Cardiac Operation; Newman et al.; Ann Thorac Surg 1995;59;1326–30; Cardiopulmonary Bypass: Perioperative Cerebral Blood Flow and Postoperative Cognitive Deficit; Venn et al.; Ann Thorac Surg 1995;59;1331–5; Long-Term Neurologic Outcome After Cardiac Operation; Sotaniemi; Ann Thorac Surg 1995;59;1336–9; and Macroemboli and Microemboli During Cardiopulmonary Bypass; Blauth; Ann Thorac Surg 1995;59;1300–3.

The patent literature includes several references relating to vascular filter devices for reducing or eliminating the potential of embolization. These and all other patents and patent applications referred to herein are hereby incorporated herein by reference in their entirety.

The following U.S. patents relate to vena cava filters: U.S. Pat. Nos. 5,549,626, 5,415,630, 5,152,777, 5,375,612, 4,793,348, 4,817,600, 4,969,891, 5,059,205, 5,324,304, 5,108,418, 4,494,531. Vena cava filters are devices that are implanted into a patient's inferior vena cava for capturing thromboemboli and preventing them from entering the right heart and migrating into the pulmonary arteries. These are generally designed for permanent implantation and are only intended to capture relatively large thrombi, typically those over a centimeter in diameter, that could cause a major pulmonary embolism. As such, these are unsuitable for temporary deployment within a patient's aorta or for capturing macroemboli or microemboli associated with adverse neurological outcomes. Vena cava filters are also not adapted for simultaneously providing arterial blood perfusion in connection with cardiopulmonary bypass.

The following U.S. patents relate to vascular filter devices: U.S. Pat. Nos. 5,496,277, 5,108,419, 4,723,549, 3,996,938. These filter devices are not of a size suitable for deployment within a patient's aorta, nor would they provide sufficient filter surface area to allow aortic blood flow at normal physiologic flow rates without an unacceptably high pressure drop across the filter. Furthermore, these filter devices are not adapted for simultaneously providing arterial blood perfusion in connection with cardiopulmonary bypass devices.

The following U.S. patents relate to aortic filters or aortic filters associated with atherectomy devices: U.S. Pat. Nos. 5,662,671, 5,769,816. The following international patent applications relate to aortic filters or aortic filters associated with atherectomy devices: WO 97/17100, WO 97/42879, WO 98/02084. The following international patent application relates to a carotid artery filter: WO 98/24377. This family of U.S. and international patents includes considerable discussion on the mathematical relationship between blood flow rate, pressure drop, filter pore size and filter area and concludes that, for use in the aorta, it is desirable for the filter mesh to have a surface area of 3–10 in$^2$, more preferably 4–9 in$^2$, 5–8 in$^2$ or 6–8 in$^2$, and most preferably 7–8 in$^2$. While these patents state that this characteristic is desirable, none of the filter structures disclosed in the drawings and description of these patents appears capable of providing a filter surface area within these stated ranges when deployed within an average-sized human aorta. Accordingly, it would be desirable to provide a filter structure or other means that solves this technical problem by increasing the effective surface area of the filter mesh to allow blood flow at normal physiologic flow rates without an unacceptably high pressure drop.

SUMMARY OF THE INVENTION

In keeping with the foregoing discussion, the present invention takes the form of a perfusion filter catheter or cannula having an embolic filter assembly mounted on an elongated tubular catheter shaft. The elongated tubular catheter shaft is adapted for introduction into a patient's ascending aorta either by a peripheral arterial approach or by a direct aortic puncture. A fine filter mesh for capturing macroemboli and/or microemboli is mounted on the embolic filter assembly. The embolic filter assembly has an undeployed state in which the filter is compressed or wrapped tightly around the catheter shaft and a deployed state in which the embolic filter assembly expands to the size of the aortic lumen and seals against the inner wall of the aorta. The embolic filter assembly can be passively or actively deployable. Various mechanisms are disclosed for both passive and active deployment of the embolic filter assembly. Optionally, an outer tube may cover the embolic filter assembly when it is in the undeployed state. Radiopaque markers and/or sonoreflective markers, may be located on the catheter and/or the embolic filter assembly. Preferably, a perfusion lumen extends through the elongated tubular catheter shaft to one or more perfusion ports upstream of the embolic filter assembly. Oxygenated blood is perfused through the perfusion lumen and any embolic materials that might be dislodged are captured in the deployed embolic filter assembly.

In order to provide a sufficient flow rate of oxygenated blood for support of all critical organ systems through the filter without excessive pressure drop, it is preferred that the surface area of the filter mesh be greater than twice the cross-sectional area of the aortic lumen, more preferably three, four, five or six times greater than luminal cross section of the aorta. Preferably, the embolic filter assembly is also configured to hold at least a majority of the filter mesh away from the aortic wall when deployed to maximize the effective filter surface area. Several possible configurations are described for the embolic filter assembly that meet these parameters. The embolic filter assembly configurations described include an elongated cone, a frustum of a cone, a trumpet-shape, a modified trumpet-shape, and helically, circumferentially and longitudinally convoluted shapes. Further configurations are described having standoff members for centering the embolic filter assembly within the aorta and for holding at least a majority of the filter mesh away from the aortic walls when deployed.

Embodiments are also described that combine the perfusion filter catheter with an aortic occlusion device, which may be a toroidal balloon, an expandable balloon or a selectively deployable external catheter flow control valve. The combined device allows percutaneous transluminal administration of cardiopulmonary bypass and cardioplegic arrest with protection from undesirable embolic events. An embodiment of the perfusion filter catheter is described having an aortic transillumination system for locating and monitoring the position and the deployment state of the catheter and the embolic filter assembly without fluoroscopy.

In use, the perfusion filter catheter is introduced into the patient's aorta with the embolic filter assembly in a collapsed state either by a peripheral arterial approach or by a direct aortic puncture. The embolic filter assembly is advanced across the aortic arch and into the ascending aorta. When the embolic filter assembly is positioned in the ascending aorta between the aortic valve and the brachiocephalic artery, the embolic filter assembly is either actively or passively deployed. The position of the catheter and the deployment state of the embolic filter assembly may be monitored using fluoroscopy, ultrasound, transesophageal echography (TEE) or aortic transillumination. Once the embolic filter assembly is deployed, oxygenated blood may be infused into the aorta through the perfusion lumen. Any potential emboli are captured by the embolic filter assembly and prevented from entering the neurovasculature or other branches downstream. After use, the embolic filter assembly is returned to the collapsed position and the catheter is withdrawn from the patient.

BRIEF DESCRIPTION OF THE DRAWINGS

FIGS. 1–3 show a perfusion filter catheter configured for retrograde deployment via a peripheral arterial access point. FIG. 1 is a cutaway perspective view of the perfusion filter catheter deployed within the aorta via femoral artery access. FIG. 2 shows the distal end of the catheter with the embolic filter assembly in a deployed state. FIG. 3 shows the distal end of the catheter with the embolic filter assembly in a collapsed state for insertion or withdrawal of the device from the patient.

FIGS. 21–23 show a method of actively deploying a circumferentially pleated embolic filter assembly on a perfusion filter catheter.

DETAILED DESCRIPTION OF THE INVENTION

Figure 4:
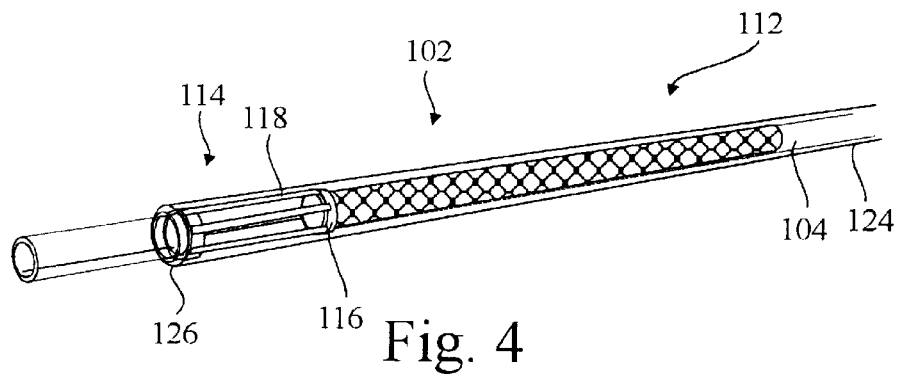
FIGS. 4–6 show a method of passively deploying an embolic filter assembly on a perfusion filter catheter.

FIGS. 1–3 show a perfusion filter catheter 100 according to the present invention configured for retrograde deployment via a peripheral arterial access point. FIG. 1 is a cutaway perspective view of the perfusion filter catheter 100 deployed within the aorta of a patient via femoral artery access. FIG. 2 shows the distal end of the catheter 100 with the embolic filter assembly 102 in a deployed state. FIG. 3 shows the distal end of the catheter with the embolic filter assembly 102' in a collapsed state for insertion or withdrawal of the device from the patient.

Referring now to FIG. 1, the perfusion filter catheter 100 includes an elongated tubular catheter shaft 104 with a proximal end 108 and distal end 110. The catheter shaft 104 is preferably extruded of a flexible thermoplastic material or a thermoplastic elastomer. Suitable materials for the catheter shaft 104 include, but are not limited to, polyvinylchloride, polyurethane, polyethylene, polypropylene, polyamides (nylons), and alloys or copolymers thereof, as well as braided, coiled or counterwound wire or filament reinforced composites. The tubular catheter shaft 104 may have a single lumen or multilumen construction. In the exemplary embodiment shown, the catheter 100 has a single perfusion lumen 106 extending from the proximal end 108 to the distal end 110 of the catheter shaft 104. The perfusion lumen 106 is open at the distal end 110 of the catheter shaft 104. The distal end 110 of the catheter shaft 104 may have a simple beveled or rounded distal edge, as shown, or it may include additional side ports or a flow diffuser to reduce jetting when oxygenated blood is infused through the perfusion lumen 106. The proximal end 108 of the elongated tubular catheter shaft 104 is adapted for connecting the perfusion lumen 106 to a cardiopulmonary bypass pump or other source of oxygenated blood using standard barb connectors or other connectors, such as a standard luer fitting (not shown). Preferably, the catheter shaft 104 is made with thin walled construction to maximize the internal diameter and therefore the flow rate of the perfusion lumen 106 for a given outside diameter and length of the catheter shaft 104. Thin walled construction also allows the outside diameter of the catheter shaft 104 to be minimized in order to reduce the invasiveness of the procedure and to reduce trauma at the insertion site. The perfusion lumen 106 should be configured to allow sufficient blood flow to preserve organ function without hemolysis or other damage to the blood. For standard cardiopulmonary support techniques, a catheter shaft 104 of 18–24 French size (6–8 mm outside diameter) is sufficient to deliver the requisite 3–4 liters of oxygenated blood to preserve organ function. For low flow cardiopulmonary support techniques, such as described in commonly owned, copending patent application Ser. No. 60/084,835, filed May 8, 1998 which is hereby incorporated by reference, the size of the catheter shaft 104 can be reduced to 9–18 French size (3–6 mm outside diameter) for delivering 0.5–3 liters of oxygenated blood to preserve organ function. The catheter shaft 104 should have a length sufficient to reach from the arterial access point where it is inserted to the ascending aorta of the patient. For femoral artery deployment, the catheter shaft 104 preferably has a length from approximately 80–120 cm.

A deployable embolic filter assembly 102 is located just proximal to the distal end 110 of the catheter shaft 104. The embolic filter assembly 102 includes a filter screen 112 made of a fine mesh material. In this exemplary embodiment and each of the other embodiments described below, the fine mesh material of the filter screen 112 may be a woven or knitted fabric, such as Dacron polyester or nylon mesh, or other textile fabrics, or it may be a nonwoven fabric, such as a spun bonded polyolefin or expanded polytetrafluoroethylene or other nonwoven materials. The fine mesh material of the filter screen 112 may be woven, knitted or otherwise formed from monofilament or multifilament fibers. The fine mesh material of the filter screen 112 may also be a fine wire mesh or a combination of wire and textile fibers. Alternatively, the fine mesh material of the filter screen 112 may be an open cell foam material. The fine mesh material of the filter screen 112 must be nontoxic and hemocompatible, that is, non-thrombogenic and non-hemolytic. Preferably, the fine mesh material of the filter screen 112 has a high percentage of open space, with a uniform pore size. The pore size of the filter screen 112 can be chosen to capture macroemboli only or to capture macroemboli and microemboli. In most cases the pore size of the filter screen 112 will preferably be in the range of 1–200 micrometers. For capturing macroemboli only, the pore size of the filter screen 112 will preferably be in the range of 50–200 micrometers, more preferably in the range of 80–100 micrometers. For capturing macroemboli and microemboli, the pore size of the filter screen 112 will preferably be in the range of 1–100 micrometers, more preferably in the range of 5–20 micrometers. In other applications, such as for treating thromboembolic disease, a larger pore size, e.g. up to 1000 micrometers (1 mm) or larger, would also be useful. In some embodiments, a combination of filter materials having different pore sizes may be used.

Alternatively or additionally the material of the filter screen in each embodiment of the filter catheter may be made of or coated with an adherent material or substance to capture or hold embolic debris which comes into contact with the filter screen within the embolic filter assembly. Suitable adherent materials include, but are not limited to, known biocompatible adhesives and bioadhesive materials or substances, which are hemocompatible and non-thrombogenic. Such materials are known to those having ordinary skill in the art and are described in, among other references, U.S. Pat. No. 4,768,523, 5,055,046, 5,066,709, 5,197,973, 5,225,196, 5,374,431, 5,578,310, 5,645,062, 5,648,167, 5,651,982, and 5,665,477. In one particularly preferred embodiment, only the upstream side of the elements of the filter screen are coated with the adherent material to positively capture the embolic debris which comes in contact with the upstream side of the filter screen after entering the filter assembly. Other bioactive substances, for example, heparin or thrombolytic agents, may be impregnated into or coated on the surface of the filter screen material or incorporated into an adhesive coating.

The embolic filter assembly 102 is movable between a collapsed state, as shown in FIG. 3, and an expanded or deployed state, as shown in FIGS. 1 and 2. The filter screen 112 may be attached directly to the catheter shaft 104 and it may constitute the entire embolic filter assembly 102, particularly if the filter screen 112 is made of a resilient or semirigid fabric that has enough body to be self-supporting in the deployed state. Generally, however, the embolic filter assembly 102 will also include a filter support structure 114, particularly if a highly flexible or flaccid material is used for the filter screen 112. The filter support structure 114 attaches and supports the filter screen 112 on the catheter shaft 104. In the illustrative embodiment of FIGS. 1–3, the filter support structure 114 is constructed with an outer hoop 116 and a plurality of struts 118 which extend approximately radially from a ring-shaped hub 126 that is mounted on the catheter shaft 104. In this case four struts 118 are shown, however, two, three or more struts 118 may be used. The open distal end 122 of the filter screen 112 is attached to the outer hoop 116 and the proximal end 120 of the filter screen 112 is sealingly attached to the catheter shaft 104. When the embolic filter assembly 102 is deployed, the outer hoop 116 of the filter support structure 114 holds the open distal end 122 of the filter screen 112 against the inner wall of the aorta, as shown in FIG. 1. To accommodate most normal adult aortas, the outer hoop 116 of the filter support structure 114 and the distal end 122 of the filter screen 112 have a diameter of approximately 2.5 to 4 cm, plus or minus 0.5 cm. Larger and smaller diameter filter support structures 114 may be made to accommodate patients with distended or Marfan syndrome aortas or for pediatric patients.

The embolic filter assembly 102 may be deployed by a passive means or by an active means. Passive means for deploying the embolic filter assembly 102 could include using the elastic memory of the filter screen 112 and/or the filter support structure 114 to deploy the embolic filter assembly 102, and/or using pressure from the blood flow in the aorta to deploy the embolic filter assembly 102. By contrast, active means for deploying the embolic filter assembly 102 could include one or more actuation members within the catheter shaft 104 for mechanically actuating the filter support structure 114 to deploy the embolic filter assembly 102 from the proximal end 108 of the catheter 100. Shape memory materials may also be used as actuation members for deploying the embolic filter assembly 102. Alternatively, active means for deploying the embolic filter assembly 102 could include one or more lumens within the catheter shaft 104 for hydraulically actuating the filter support structure 114 to deploy the embolic filter assembly 102. Passive means may be used to augment the action of the active deployment means. As shown in FIG. 3, an outer tube 124 may be provided to cover the embolic filter assembly 102 when it is in the collapsed state in order to create a smooth outer surface for insertion and withdrawal of the catheter 100 and to prevent premature deployment of the embolic filter assembly 102, particularly if passive deployment means are used.

The perfusion filter catheter 100 is prepared for use by folding or compressing the embolic filter assembly 102 into a collapsed state within the outer tube 124, as shown in FIG. 3. The distal end 110 of the catheter 100 is inserted into the aorta in a retrograde fashion. Preferably, this is done through a peripheral arterial access, such as the femoral artery or subclavian artery, using the Seldinger technique or an arterial cutdown. Alternatively, the catheter 100 may be introduced directly through an incision into the descending aorta after the aorta has been surgically exposed. The embolic filter assembly 102 is advanced up the descending aorta and across the aortic arch while in the collapsed state. The position of the catheter 100 may be monitored using fluoroscopy or ultrasound, such as transesophageal echography (TEE). Appropriate markers, which may include radiopaque markers and/or sonoreflective markers, may be located on the distal end 110 of the catheter 100 and/or the embolic filter assembly 102 to enhance imaging and to show the position of the catheter 100 and the deployment state of the embolic filter assembly 102. When the distal end 110 of the catheter 100 is positioned in the ascending aorta between the aortic valve and the brachiocephalic artery, the outer tube 124 is withdrawn and the embolic filter assembly 102 is deployed, as shown in FIG. 3. Optionally, a distal portion of the catheter shaft 104 may be precurved to match the curvature of the aortic arch to aid in placement and stabilization of the catheter 100 and the embolic filter assembly 102 within the aorta. Once the embolic filter assembly 102 is deployed, oxygenated blood may be infused through the perfusion lumen 106 to augment cardiac output of the beating heart or to establish cardiopulmonary bypass so that the heart can be arrested. Any potential emboli are captured by the filter screen 112 and prevented from entering the neurovasculature or other branches downstream. After use, the embolic filter assembly 102 is returned to the collapsed position and the catheter 100 is withdrawn from the patient.

Preferably, the embolic filter assembly 102 is configured so that, when it is in the deployed state, at least a majority of the filter screen 112 is held away from the aortic walls so that flow through the pores of the filter screen 112 is not occluded by contact with the aortic wall. In addition, this also assures that blood flow into the side branches of the aorta will not be obstructed by the filter screen 112. In this way, each side branch of the aorta will receive the benefit of flow through the full surface area of the filter screen 112 so that blood flow is not restricted by the area of the ostium of each side branch. In the illustrative embodiment of FIGS.

1–3, the filter screen 112 has a roughly conical shape with an open distal end 122. The conical shape holds the fine mesh material of the filter screen 112 away from the aortic walls and away from the ostia of the side branches so that blood can flow freely through the pores of the filter screen 112.

Figure 5:
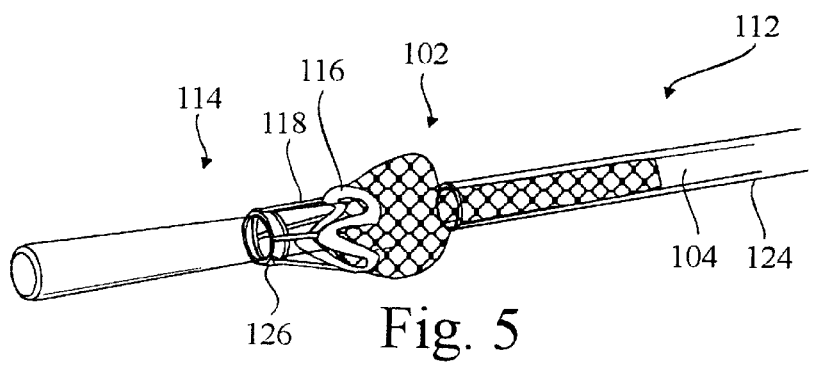
Figure 6:
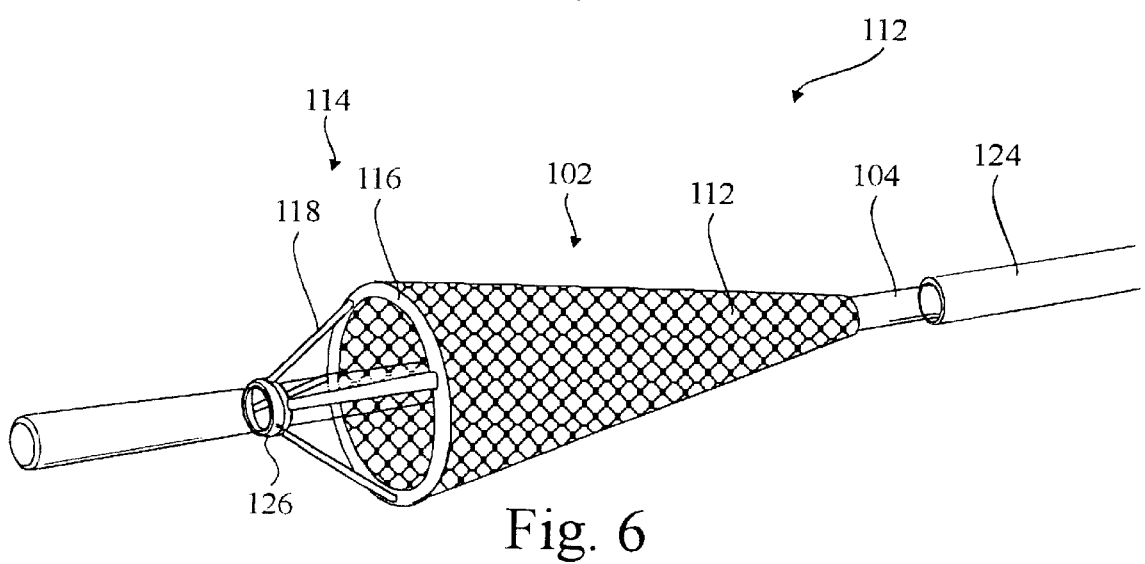

Deployment of the embolic filter assembly 102 can be accomplished passively or actively. FIGS. 4–11 show various methods of passively deploying the embolic filter assembly 102 and FIGS. 12–23 show various methods of actively deploying the embolic filter assembly 102. FIGS. 4–6 show one method of passively deploying the embolic filter assembly 102. In this exemplary embodiment, the outer hoop 116 and the struts 118 of the filter support structure 114 are made of an elastic or superelastic metal or polymer, for example a superelastic nickel/titanium alloy, which is easily deformed into the collapsed state and which expands passively from the collapsed state to the deployed state. To place the embolic filter assembly 102 in the collapsed position shown in FIG. 4, the struts 118 are folded back in the proximal direction and the outer hoop 116 is folded against the catheter shaft 104 along with the material of the filter screen 112. The outer tube 124 is placed over the folded embolic filter assembly 102 to hold it in the collapsed position. Once the perfusion filter catheter 100 is in position within the patient's aorta, the outer tube 124 is pulled back, as shown in FIG. 5, to release the folded embolic filter assembly 102. The outer hoop 116 and struts 118 expand the filter screen 112 to its deployed position, shown in FIG. 6, and hold the open distal end 122 of the filter screen 112 against the inner wall of the aorta, as shown in FIG. 1. After use, the embolic filter assembly 102 is returned to the collapsed position by advancing the outer tube 124 distally over the filter screen 112 and the filter support structure 114, then the catheter 100 is withdrawn from the patient.

FIGS. 7, 7A, 8 and 8A show another method of passively deploying an embolic filter assembly 132 on a perfusion filter catheter 130. In this embodiment, the filter support structure includes a plurality of struts 136 which are hinged or flexibly attached at their inner, proximal ends to the catheter shaft 134. The struts 136 may be made of either a metal or a polymer. The distal end 138 of the filter screen 140 is attached to the struts 136 along an outer, distal portion of the struts 136. The proximal end 146 of the filter screen 140 is sealingly attached to the catheter shaft 134. The portion of the filter screen 140 attached to the struts 136 forms a skirt 142 along the distal edge of the filter assembly 132. The remaining portion of the filter screen 140 forms a filter pocket 144 along the proximal end of the filter assembly 132. The skirt 142 and the filter pocket 144 may be made of the same filter material or they may be made of different filter materials having different porosities. The skirt 142 of the filter screen 140 may even be made of a nonporous material.

Figure 7:
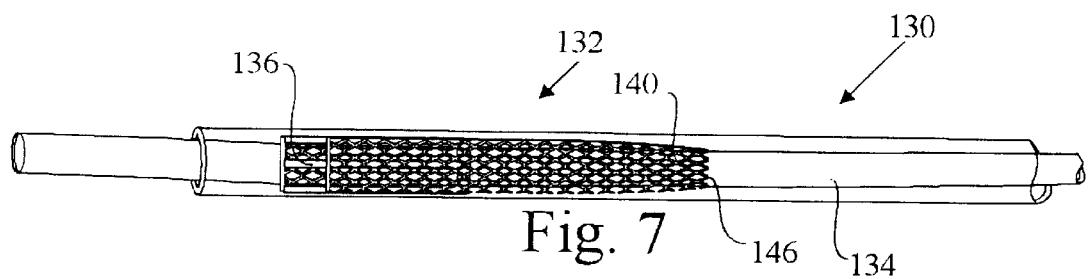
FIGS. 7, 7A, 8 and 8A show a flow-assisted method of passively deploying an embolic filter assembly on a perfusion filter catheter.
Figure 7A:
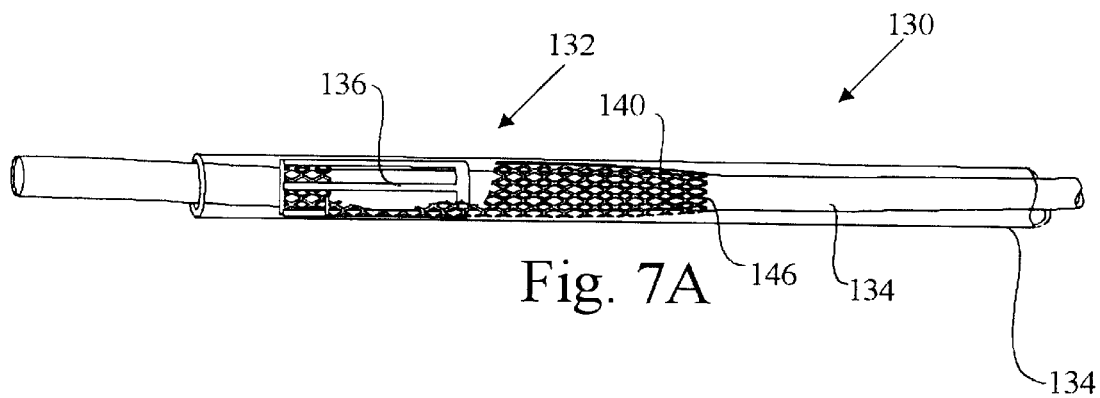
Figure 8:
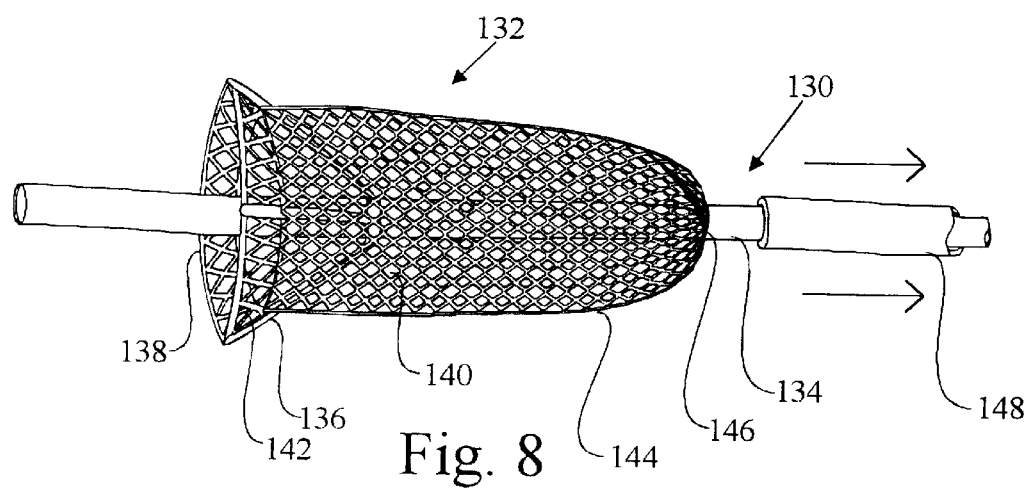
Figure 8A:
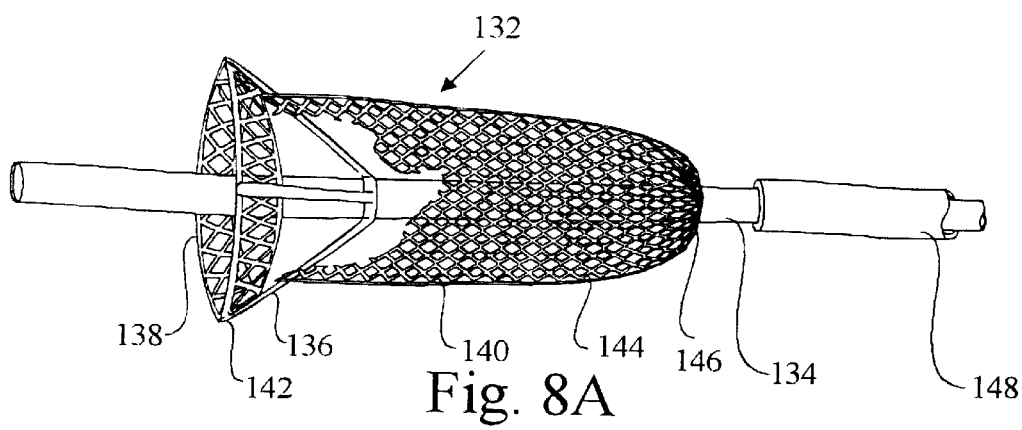

The embolic filter assembly 132 is folded into the collapsed position shown in FIG. 7 by folding the struts 136 in the distal direction so they lie against the catheter shaft 134. FIG. 7A is a cutaway view of the catheter 130 with the embolic filter assembly 132 in the collapsed position. The material of the filter screen 140 is folded around or in between the struts 136. The outer tube 148 is placed over the folded embolic filter assembly 132 to hold it in the collapsed position. Once the perfusion filter catheter 130 is in position within the patient's aorta, the outer tube 148 is pulled back, as shown in FIG. 8, to release the folded embolic filter assembly 132. Blood flow within the aorta catches the skirt 142 of the filter screen 140 and forces the embolic filter assembly 132 to open into the deployed position shown in FIG. 8. FIG. 8A is a cutaway view of the catheter 130 with the embolic filter assembly 132 in the deployed position. Optionally, the struts 136 may be resiliently biased toward the deployed position to assist in passive deployment of the embolic filter assembly 132. As the embolic filter assembly 132 is passively opened by the blood flow, the skirt 142 of the filter screen 140 naturally and atraumatically seals against the aortic wall. The passive deployment of the skirt 142 also naturally compensates for patient-to-patient variations in aortic luminal diameter. The filter pocket 144 of the embolic filter assembly 132 is held away from the aortic walls and away from the ostia of the side branches so that blood can flow freely through the pores of the filter screen 140.

Figure 9:
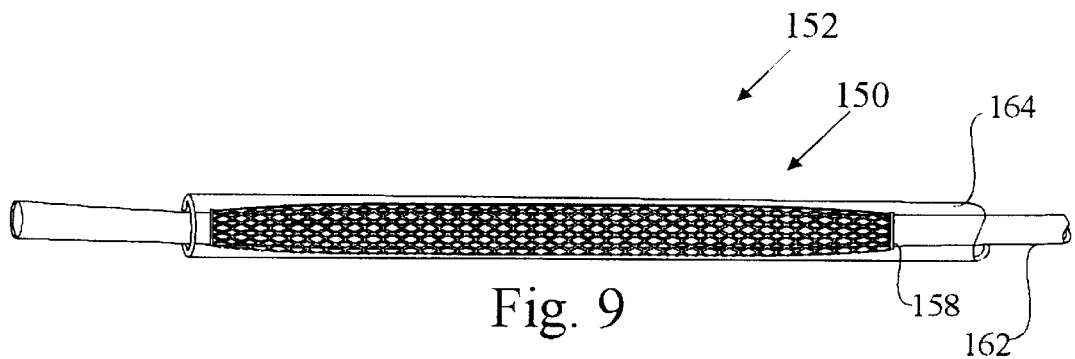
FIGS. 9–11 show a method of passively deploying a self-expanding and self-supporting embolic filter assembly on a perfusion filter catheter.
Figure 10:
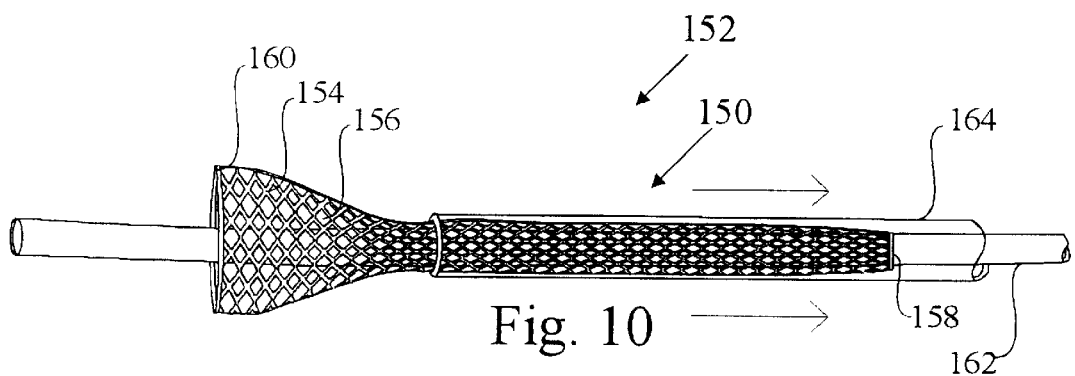
Figure 11:
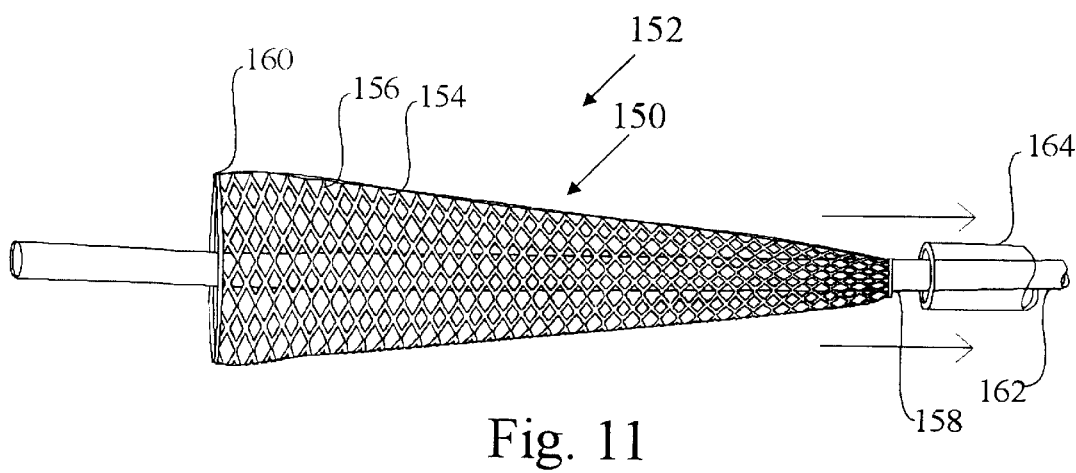

FIGS. 9–11 show another method of passively deploying an embolic filter assembly 152 on a perfusion filter catheter 150. In this embodiment, the filter screen 154 is self-expanding and self-supporting, so no separate filter support structure is needed. Preferably, the embolic filter assembly 152 includes resilient wires or filaments 156 that are interwoven with the fibers of the filter screen 154. Alternatively, the resilient wires or filaments 156 may be attached to the interior or exterior surface of the filter screen 154 fabric. The resilient wires or filaments 156 may be made of either a polymer or a metal, such as an elastic or superelastic alloy. In one preferred embodiment, the resilient wires or filaments 156, and preferably the fibers of the filter screen 154 as well, are woven at an angle to the longitudinal axis of the embolic filter assembly 152, so that the embolic filter assembly 152 can expand and contract in diameter by changing the angle of the wires or filaments 156. Generally, as the embolic filter assembly 152 expands in diameter, the angle between the wires or filaments 156 and the longitudinal axis of the embolic filter assembly 152 increases and the embolic filter assembly 152 may also foreshorten. The resilient wires or filaments 156 urge the embolic filter assembly 152 to expand to the deployed position. The proximal end 158 of the filter screen 154 is sealingly attached to the catheter shaft 162.

The perfusion filter catheter 150 is shown in FIG. 9 with the embolic filter assembly 152 compressed into the collapsed position. The embolic filter assembly 152 compresses in diameter smoothly without folding as the resilient wires or filaments 156 and the fibers of the filter screen 154 decrease their angle with respect to the longitudinal axis of the embolic filter assembly 152. An outer tube 164 holds the embolic filter assembly 152 in the collapsed position. Once the perfusion filter catheter 150 is in position within the patient's aorta, the outer tube 164 is pulled back, which allows the embolic filter assembly 152 to expand, as shown in FIG. 10. As the embolic filter assembly 152 expands, the angle between the wires or filaments 156 and the longitudinal axis of the embolic filter assembly 152 increases and the embolic filter assembly 152 foreshortens slightly. FIG. 11 shows the embolic filter assembly 152 fully expanded in the deployed position. The resilient wires or filaments 156 are preformed so that, when deployed, the filter screen 154 has a roughly conical shape with an open distal end 160. The conical shape holds the filter screen 154 away from the aortic walls and away from the ostia of the side branches so that blood can flow freely through the pores of the filter screen 154. The distal end 160 of the embolic filter assembly 152 seals against the aortic wall. The self-expanding aspect of the embolic filter assembly 152 naturally compensates for patient-to-patient variations in aortic luminal diameter.

In alternate embodiments, the resilient wires or filaments 156 may be preformed to other geometries so that the filter screen 154 of the embolic filter assembly 152 assumes a different configuration when deployed, including each of the other configurations discussed within this patent specification.

Figure 12:
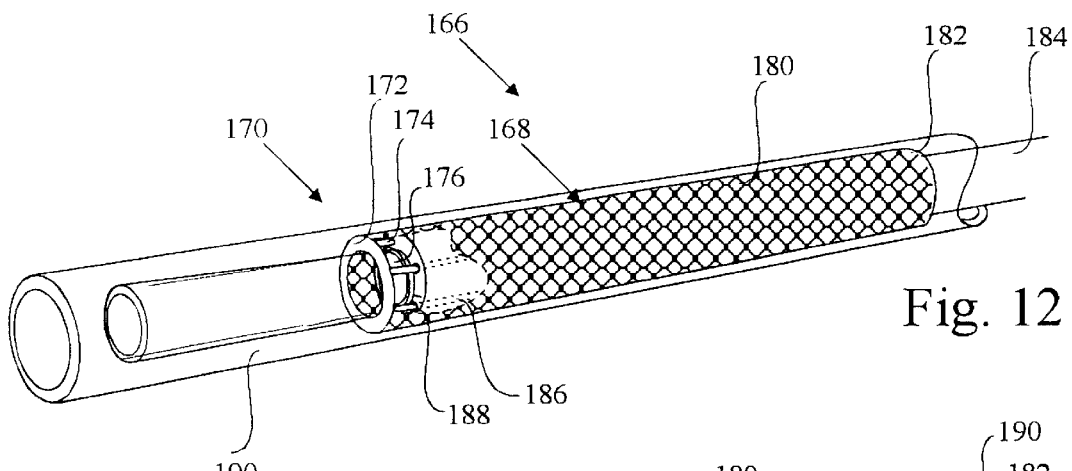
FIGS. 12–14 show a method of actively deploying an embolic filter assembly with a collapsible outer hoop and a plurality of actuation wires.
Figure 13:
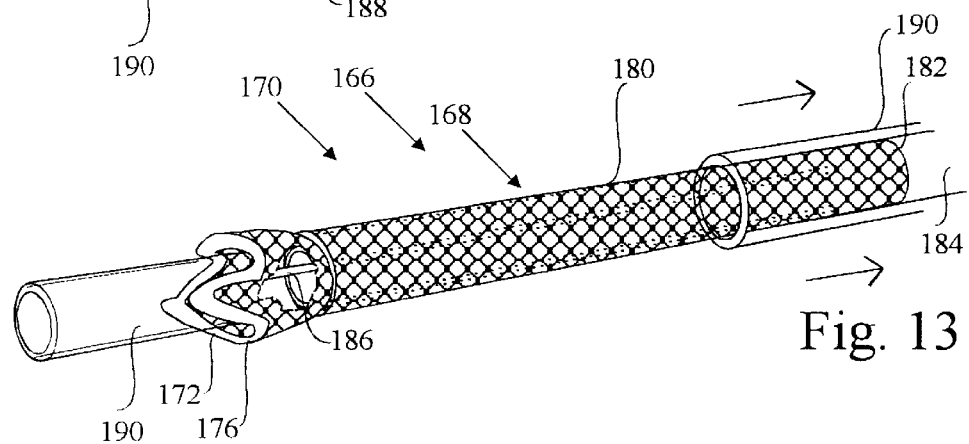
Figure 14:
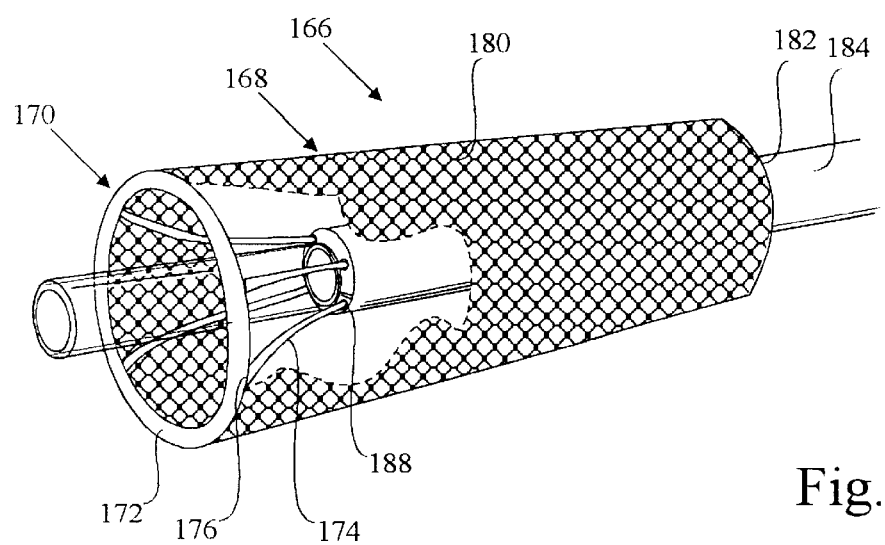

FIGS. 12–14 show one method of actively deploying an embolic filter assembly 168 on a perfusion filter catheter 166. In this exemplary embodiment, the filter support structure 170 includes a collapsible outer hoop 172 and a plurality of actuation wires 174. The distal end 176 of the filter screen 180 is attached to the outer hoop 172 and the proximal end 182 of the filter screen 180 is sealingly attached to the catheter shaft 184. The actuation wires 174 are slidably received within actuation wire lumens 186 located in the outer wall of the catheter shaft 184. The actuation wires 174 exit the actuation wire lumens 186 through side ports 188 located near the distal end of the catheter shaft 184. The actuation wires 174 and the outer hoop 172 are each made of a resilient polymer or a metal, such as stainless steel, nickel/titanium alloy or the like.

The perfusion filter catheter 166 is shown in FIG. 12 with the embolic filter assembly 168 compressed into the collapsed position. The actuation wires 174 are withdrawn into the actuation wire lumens 186 through the side ports 188 and the outer hoop 172 is folded or collapsed against the catheter shaft 184. The material of the filter screen 180 is folded or collapsed around the catheter shaft 184. An outer tube 190 covers the embolic filter assembly 168 in the collapsed position to facilitate insertion of the catheter 166. Once the perfusion filter catheter 150 is in position within the patient's aorta, the outer tube 190 is pulled back to expose the embolic filter assembly 152. Then, the actuation wires 174 are advanced distally to expand the outer hoop 172 and the filter screen 180, as shown in FIG. 13. FIG. 14 shows the embolic filter assembly 168 fully expanded in the deployed position. In this exemplary embodiment, the filter screen 180 is configured as a frustum of a cone with an open distal end 176. The outer hoop 172 at the distal end 176 of the filter screen 180 seals against the aortic wall.

Figure 15:
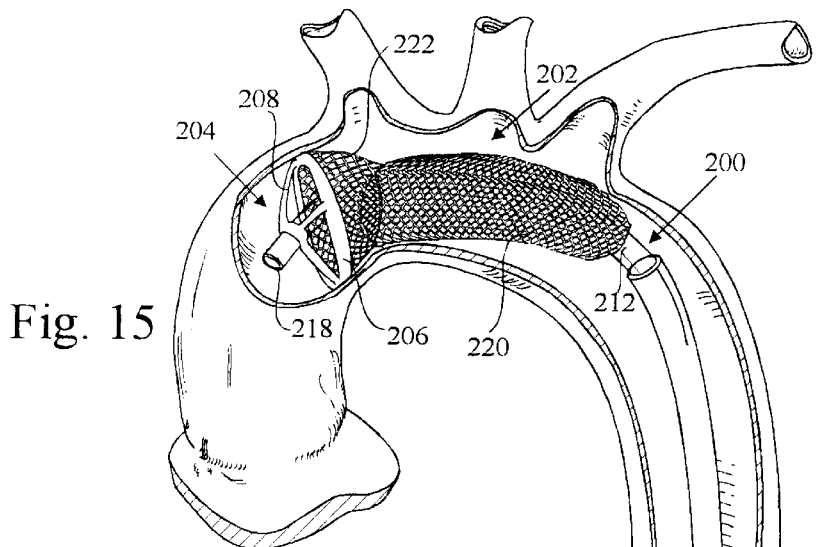
FIGS. 15–17 show a method of actively deploying an embolic filter assembly with an inflatable filter support structure.
Figure 16:
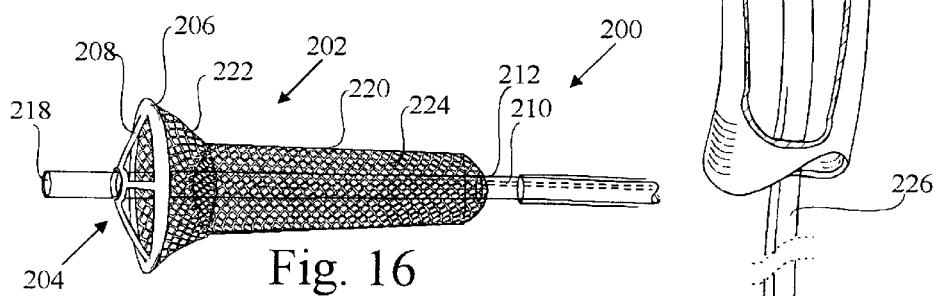
Figure 17:
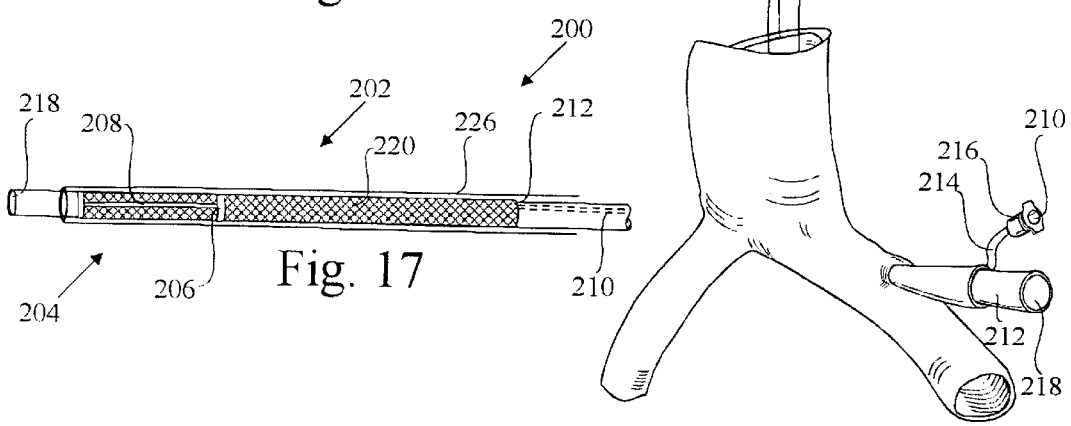

FIGS. 15–17 show another method of actively deploying an embolic filter assembly 202 on a perfusion filter catheter 200. In this embodiment, the filter support structure 204 includes an outer hoop 206 and a plurality of struts 208, which are all interconnected hollow tubular members. Preferably, the outer hoop 206 and the struts 208 are made of a flexible polymeric material. The filter support structure 204 is connected to an inflation lumen 210, which parallels the perfusion lumen 218 within the catheter shaft 212. At its proximal end, the inflation lumen 210 branches off from the catheter shaft 212 to a side arm 214 with a luer fitting 216 for connecting to a syringe or other inflation device. By way of example, this embodiment of the embolic filter assembly 202 is shown with a trumpet-shaped filter screen 220. The filter screen 220 includes a skirt portion 222 extending distally from a proximal, filter pocket 224. The skirt portion 222 is in the shape of a frustum of a cone with an open distal end, which is attached to the outer hoop 206. The filter pocket 224 is roughly cylindrical in shape with a closed proximal end, which is sealingly attached to the catheter shaft 212. The skirt 222 and the filter pocket 224 may be made of the same filter material or they may be made of different filter materials having different porosities. The skirt 222 of the filter screen 220 may even be made of a nonporous material.

The perfusion filter catheter 200 is shown in FIG. 17 with the embolic filter assembly 202 folded into a collapsed position. The outer hoop 206 and the struts 208 of the filter support structure 204 are deflated and the material of the filter screen 220 is folded or collapsed around the catheter shaft 212. An outer tube 226 covers the embolic filter assembly 202 in the collapsed position to facilitate insertion of the catheter 200. Optionally, the outer tube 226 may have a slit or a weakened longitudinal tear line along its length to facilitate removal of the outer tube 226 over the side arm 214 at the proximal end of the catheter 200. Once the perfusion filter catheter 200 is in position within the patient's aorta, the outer tube 226 is pulled back to expose the embolic filter assembly 202. Then, the embolic filter assembly 202 is deployed by inflating the outer hoop 206 and the struts 208 with fluid injected through the inflation lumen 210 to actively expand the filter support structure 204, as shown in FIG. 16. When the embolic filter assembly 202 is deployed, the outer hoop 206 of the filter support structure 204 seals against the inner wall of the aorta, as shown in FIG. 15. Preferably, at least the outer wall of the outer hoop 206 is somewhat compliant when inflated in order to compensate for patient-to-patient variations in aortic luminal diameter.

Figure 18:
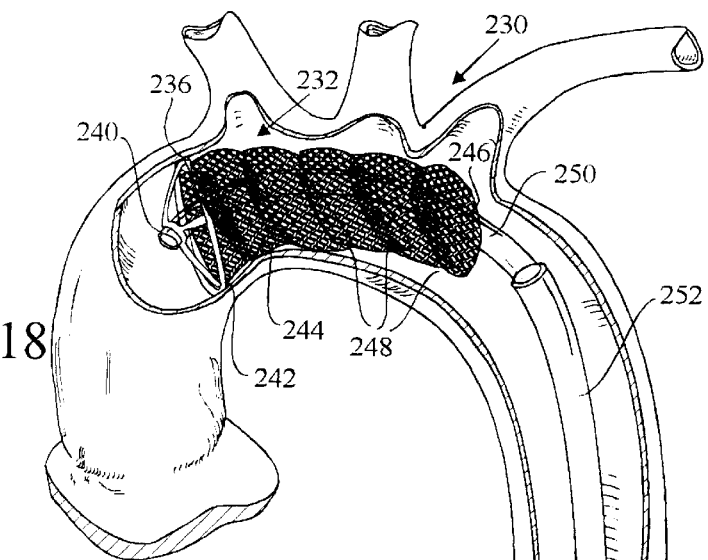
FIGS. 18–20 show a method of actively deploying a spiral fluted embolic filter assembly by twisting or furling the embolic filter assembly around an inner catheter shaft.
Figure 19:
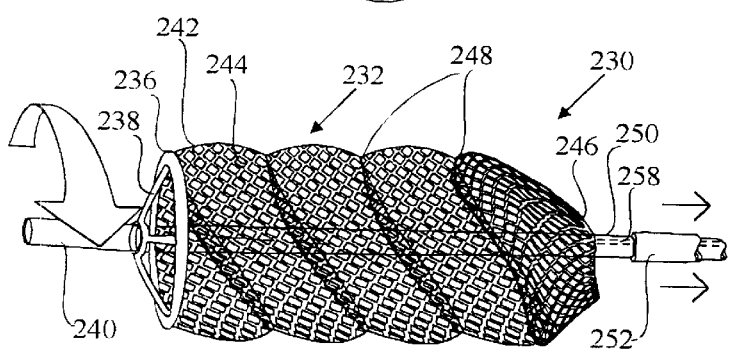
Figure 20:
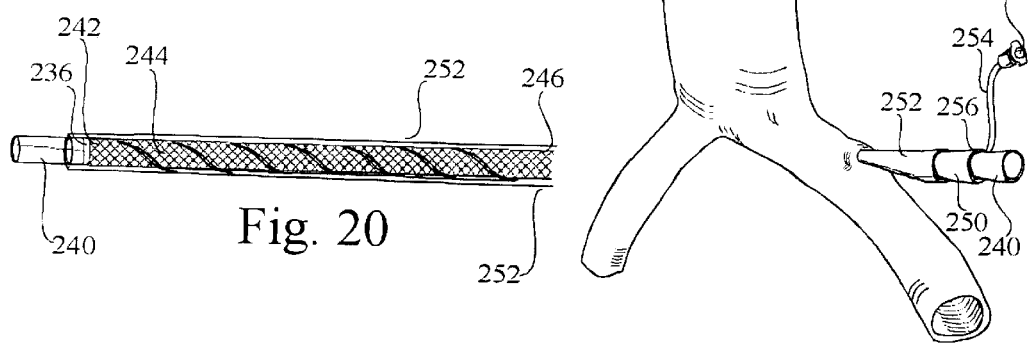

FIGS. 18–20 show another method of actively deploying an embolic filter assembly 232 on a perfusion filter catheter 230. In this embodiment, the filter support structure 234 includes an outer hoop 236 and a plurality of struts 238, which are connected to an inner catheter shaft 240. The outer hoop 236 and the struts 238 may be made of a resilient polymer or metal, for example a superelastic nickel/titanium alloy. The distal end 242 of the filter screen 244 is attached to the outer hoop 236. The proximal end 246 of the filter screen 244 is sealingly attached to an outer catheter shaft 250. The inner catheter shaft 240 is slidably and rotatably received within the outer catheter shaft 250. Preferably, the filter screen 244 has one or more spiral grooves or flutes 248 that wind helically around the filter screen 244.

The embolic filter assembly 232 is folded into the collapsed position shown in FIG. 20 by extending and rotating the inner catheter shaft 240 in a first direction with respect to the outer catheter shaft 250. This collapses the filter support structure 234 back against the inner catheter shaft 240 and furls the filter screen 244 around the inner catheter shaft 240. The spiral flutes 248 in the filter screen 244 help it to collapse smoothly around the inner catheter shaft 240. An outer tube 252 covers the embolic filter assembly 232 in the collapsed position to facilitate insertion of the catheter 230. Once the perfusion filter catheter 230 is in position within the patient's aorta, the outer tube 252 is pulled back to expose the embolic filter assembly 232. Then, the embolic filter assembly 232 is deployed by rotating the inner catheter shaft 240 in the opposite direction with respect to the outer catheter shaft 250 and allowing it to retract slightly, as shown in FIG. 19. The filter support structure 234 and the filter screen 244 will expand within the aorta and the distal end 242 of the filter screen 244 will seal against the aortic wall, as shown in FIG. 18. When it is in the deployed position, the spiral flutes 248 of the embolic filter assembly 232 hold most of the filter screen 244 away from the aortic walls and away from the ostia of the side branches so that blood can flow freely through the pores of the filter screen 244. After use, the embolic filter assembly 232 is returned to the collapsed position as described above and the catheter 230 is withdrawn from the patient.

The coaxial arrangement of the inner catheter shaft 240 and the outer catheter shaft 250 in this embodiment of the perfusion filter catheter 230 creates an annular space that can optionally be used as a lumen 258 to aspirate potential emboli that are captured by the filter screen 244. To facilitate this, a side arm 254 with a luer fitting and a sliding hemostasis valve 256 may be added to the proximal end of the outer catheter shaft 250, as shown in FIG. 18.

FIGS. 21–23 show another method of actively deploying an embolic filter assembly 262 on a perfusion filter catheter 260. In this embodiment, the filter support structure 234 includes an outer hoop 266 and a plurality of struts 268, which are connected to an inner catheter shaft 270. The outer hoop 266 and the struts 268 may be made of a resilient polymer or metal, for example a superelastic nickel/titanium alloy. The distal end 272 of the filter screen 274 is attached to the outer hoop 266. The proximal end 276 of the filter screen 274 is sealingly attached to an outer catheter shaft 280. The inner catheter shaft 270 is slidably received within the outer catheter shaft 280. Preferably, the filter screen 274 has a series of circumferential pleats 278 that give the filter screen 274 an accordion appearance.

The embolic filter assembly 262 is folded into the collapsed position shown in FIG. 23 by extending the inner catheter shaft 270 distally with respect to the outer catheter shaft 280. This collapses the filter support structure 264 back against the inner catheter shaft 270 and collapses the circumferential pleats 248 of the filter screen 274 against the inner catheter shaft 270. An outer tube 282 covers the embolic filter assembly 262 in the collapsed position to facilitate insertion of the catheter 260. Once the perfusion filter catheter 260 is in position within the patient's aorta, the outer tube 282 is pulled back to expose the embolic filter assembly 262. Then, the embolic filter assembly 262 is deployed by retracting the inner catheter shaft 270 proximally with respect to the outer catheter shaft 280, as shown in FIG. 22. The filter support structure 264 and the filter screen 274 will expand within the aorta and the distal end 272 of the filter screen 274 will seal against the aortic wall, as shown in FIG. 21. When it is in the deployed position, the circumferential pleats 278 of the embolic filter assembly 262 hold the majority of the filter screen 274 away from the aortic walls and away from the ostia of the side branches so that blood can flow freely through the pores of the filter screen 274. After use, the embolic filter assembly 262 is returned to the collapsed position as described above and the catheter 260 is withdrawn from the patient.

As with the previous embodiment, the coaxial arrangement of the inner catheter shaft 270 and the outer catheter shaft 280 in this embodiment of the perfusion filter catheter 260 creates an annular space that can optionally be used as a lumen 288 to aspirate potential emboli that are captured by the filter screen 274. To facilitate this, a side arm 284 with a luer fitting and a sliding hemostasis valve 286 may be added to the proximal end of the outer catheter shaft 280, as shown in FIG. 21.

Active deployment of the embolic filter assembly can also be accomplished with any of the preceding embodiments by using shape memory materials, such as a nickel/titanium alloy, to construct the filter support structure and/or the actuation members. The transition temperature of the shape memory material should be chosen to be close to normal body temperature so that extreme temperature variations will not be necessary for deployment. The shape memory material of the filter support structure should be annealed in the deployed position to confer a shape memory in this configuration. Then, the embolic filter assembly should be cooled below the transition temperature of the shape memory material, so that the filter support structure is malleable and can be shaped into a collapsed position. Depending on the transition temperature, this can be done at room temperature or in iced saline solution. If desired, an outer tube can be placed over the embolic filter assembly to facilitate catheter insertion and to avoid premature deployment. Once the perfusion filter catheter is in position within the patient's aorta, the outer tube is pulled back to expose the embolic filter assembly and the filter support structure is heated above the transition temperature to deploy the embolic filter assembly. Depending on the transition temperature of the shape memory material, the filter support structure can be passively heated by body heat (accounting, of course, for decreased body temperature during hypothermic cardiopulmonary support methods) or it can be self-heated by applying an electrical current through the filter support structure. When heated, the filter support structure expands to its annealed configuration within the aorta. After use, the embolic filter assembly is returned to the collapsed position by advancing the outer tube distally over the filter screen and the filter support structure, then the catheter is withdrawn from the patient.

The foregoing examples of the perfusion filter catheter of the present invention showed retrograde deployment of the device within the aorta via femoral artery access. Each of the described embodiments of the perfusion filter catheter can also be adapted for retrograde deployment via subclavian artery access or for antegrade or retrograde deployment via direct aortic puncture.

Figure 24:
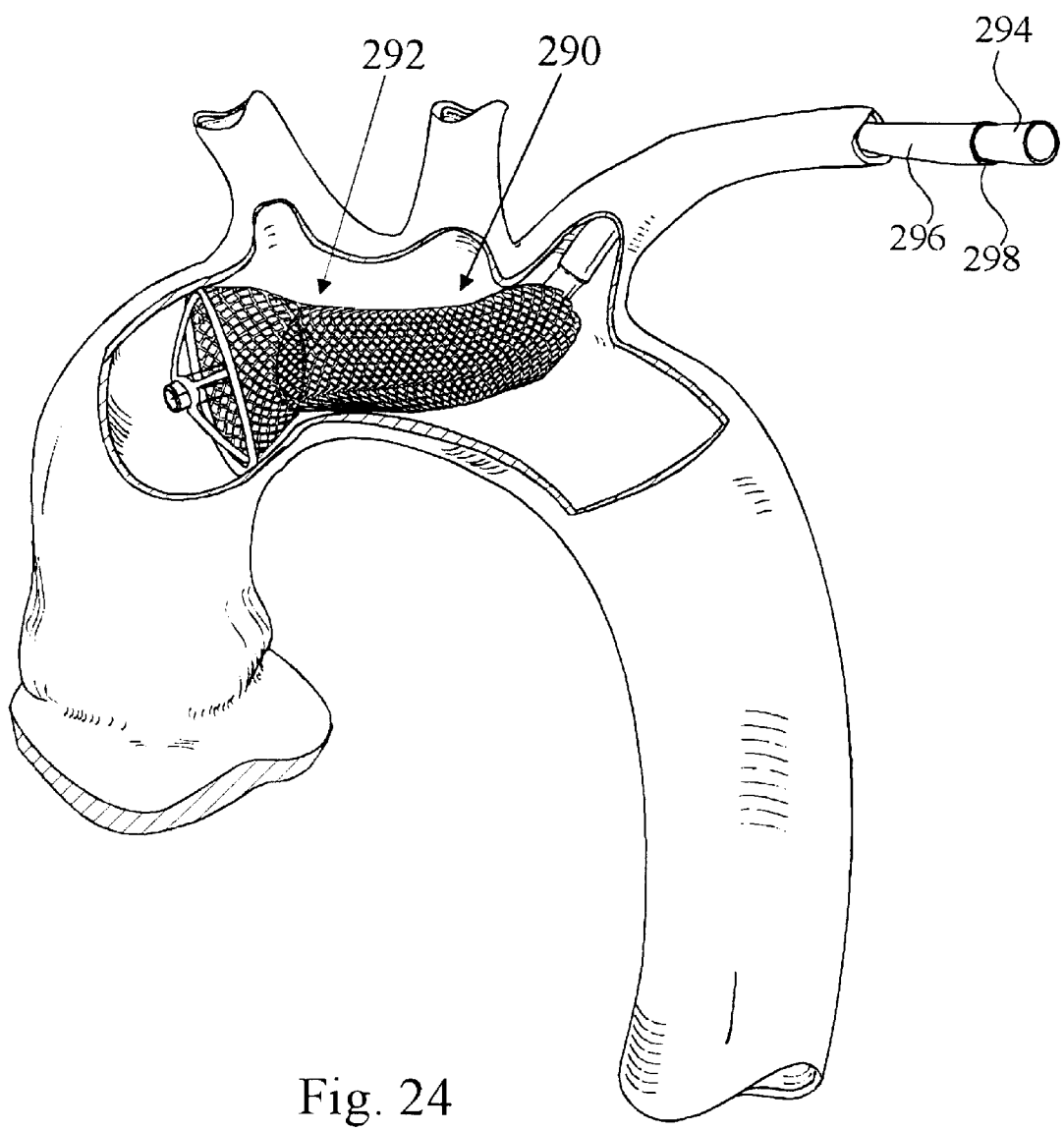
FIG. 24 shows a perfusion filter catheter adapted for retrograde deployment via subclavian artery access.

FIG. 24 shows a perfusion filter catheter 290 which is adapted for retrograde deployment via subclavian artery access. In this exemplary embodiment, the perfusion filter catheter 290 is depicted with a trumpet-style, passively-deployed embolic filter assembly 292. Because it is intended for subclavian artery access, the perfusion filter catheter 290 has a tubular catheter shaft 294 with a length of approximately 60–90 cm. Because of the shorter length, as compared to the femoral version of the catheter, the outside diameter of the catheter shaft 294 can be reduced to 12–18 French size (4–6 mm outside diameter) for delivering the 3–4 liters of oxygenated blood needed to preserve organ function. The reduced diameter of the catheter shaft 294 is especially advantageous for subclavian artery delivery of the catheter 290. To further reduce the size of the catheter system for subclavian or femoral artery delivery, the outer tube 296 may be adapted for use as an introducer sheath by the addition of an optional hemostasis valve 298 at the proximal end of the outer tube 296. This eliminates the need for a separate introducer sheath for introducing the catheter 290 into the circulatory system.

In use, the perfusion filter catheter 290 is introduced into the subclavian artery with the embolic filter assembly 292 in a collapsed state within the outer tube 296, using the Seldinger technique or an arterial cutdown. The embolic filter assembly 292 is advanced across the aortic arch while in the collapsed state. The position of the catheter 292 may be monitored using fluoroscopy or ultrasound, such as transesophageal echography (TEE). Radiopaque markers and/or sonoreflective markers, may be located on the catheter 290 and/or the embolic filter assembly 292 to enhance imaging and to show the position of the catheter 290 and the deployment state of the embolic filter assembly 292. When the distal end of the catheter 290 is positioned in the ascending aorta between the aortic valve and the brachiocephalic artery, the outer tube 296 is withdrawn and the embolic filter assembly 292 is either actively or passively deployed, as shown in FIG. 24. Once the embolic filter assembly 292 is deployed, oxygenated blood may be infused into the aorta through the tubular catheter shaft 294. Any potential emboli are captured by the embolic filter assembly 292 and prevented from entering the neurovasculature or other branches downstream. After use, the embolic filter assembly 292 is returned to the collapsed position and the catheter 290 is withdrawn from the patient.

Retrograde deployment of the perfusion filter catheter 290 via direct aortic puncture is quite similar to introduction via subclavian artery access, except that the catheter 290 is introduced directly into the descending aorta after it has been surgically exposed, for example during open-chest or minimally invasive cardiac surgery. Because of the direct aortic insertion, the length and the diameter of the catheter shaft 294 may be further reduced.

Figure 25:
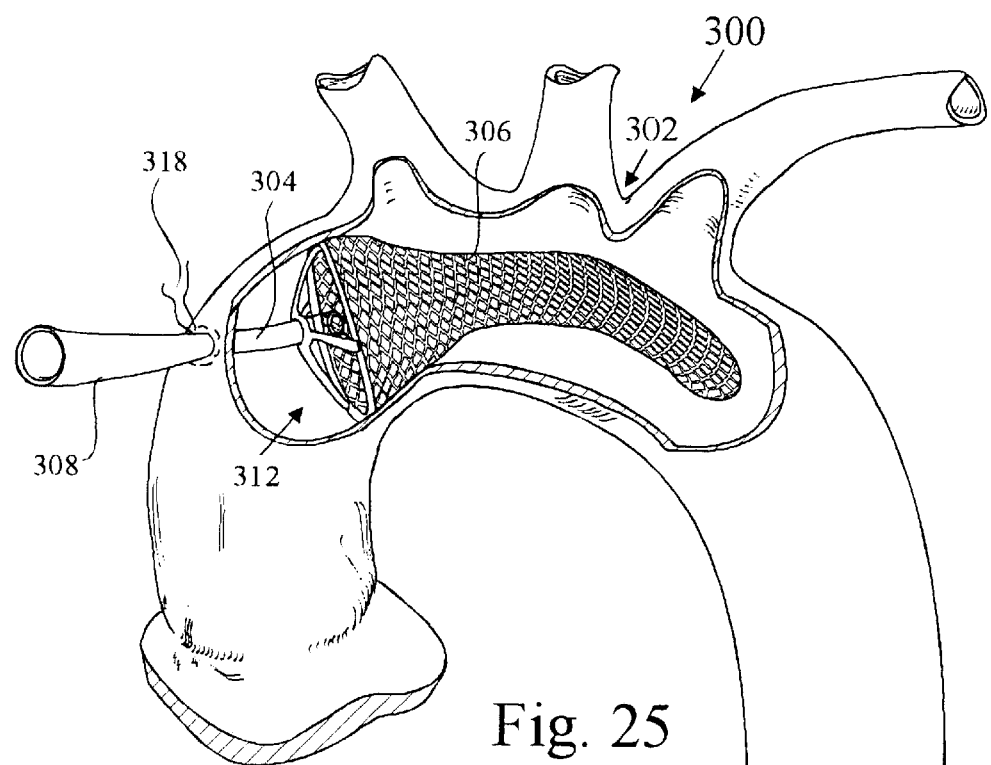
FIGS. 25–27 show a perfusion filter catheter adapted for antegrade deployment via direct aortic puncture.
Figure 26:
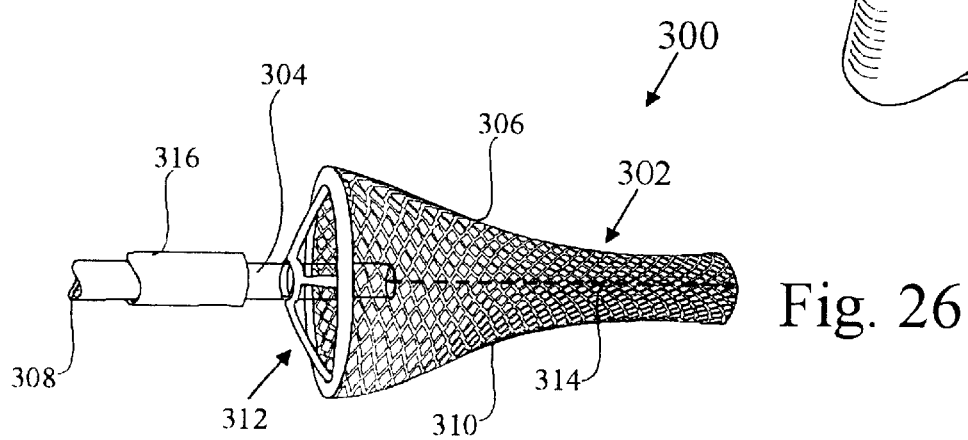
Figure 27:
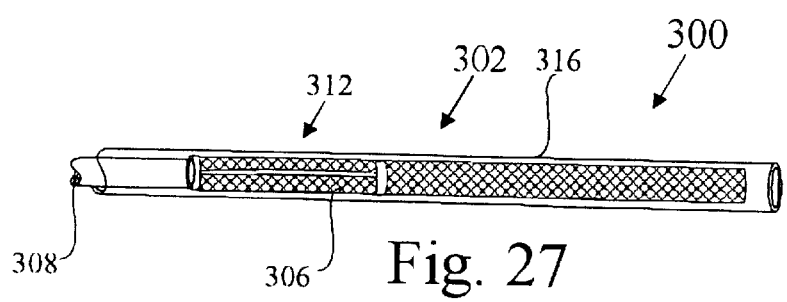

FIGS. 25–27 show a perfusion filter catheter 300 which is adapted for antegrade deployment via direct aortic puncture. In this exemplary embodiment, the perfusion filter catheter 300 is depicted with a hybrid-style embolic filter assembly 302, which is a compromise between the conical filter screen and the trumpet-style filter screen previously described. Because the catheter 300 is introduced directly into the ascending aorta, the catheter shaft 304 can be reduced to a length of approximately 20–60 cm and an outside diameter of approximately 12–18 French size (4–6 mm outside diameter) for delivering the 3–4 liters of oxygenated blood needed to preserve organ function during cardiopulmonary bypass. An important modification that must be made to the catheter 300 for antegrade deployment is that the perfusion port or ports 306 which connect to the perfusion lumen 308 must exit the catheter shaft 304 proximal to the filter screen 310 so that fluid flow will come from the upstream side of the embolic filter assembly 302. The catheter shaft 304 need not extend all the way to the distal end of the filter screen 310. The filter screen 310 may be entirely supported by the filter support structure 312, particularly if the embolic filter assembly 302 is to be passively deployed. Alternatively, a small diameter filter support member 314 may extend from the catheter shaft 304 to the distal end of the filter screen 310. If the embolic filter assembly 302 is intended to be actively deployed, the filter support member 314 may be slidably and/or rotatably received within the catheter shaft 304. Either of these configurations allows the embolic filter assembly 302 to be folded or compressed to a size as small as the diameter of the catheter shaft 304 to facilitate insertion of the catheter 300. Optionally, an outer tube 316 may be placed over the folded embolic filter assembly 302 to hold it in the collapsed position.

In use, the ascending aorta of the patient is surgically exposed, using open-chest or minimally invasive surgical techniques. A purse string suture 318 is placed in the ascending aorta and an aortotomy incision is made through the aortic wall. The catheter 300, with the embolic filter assembly 302 in the collapsed position within the outer tube 316, is inserted through the aortotomy and advanced antegrade into the aortic arch. When the proximal end of the embolic filter assembly 302 is positioned in the ascending aorta between the aortic valve and the brachiocephalic artery, the outer tube 316 is withdrawn and the embolic filter assembly 302 is either actively or passively deployed, as shown in FIG. 25. Once the embolic filter assembly 302 is deployed, oxygenated blood may be infused into the aorta through the tubular catheter shaft 304. Any potential emboli are captured by the embolic filter assembly 302 and prevented from entering the neurovasculature or other branches downstream. After use, the embolic filter assembly 302 is returned to the collapsed position, the catheter 300 is withdrawn from the patient, and the purse string suture 318 is tightened to close the aortotomy.

In general, each of the passive and active deployment methods described above may be used interchangeably or together in combinations with each of the embodiments of the perfusion filter catheter and each of catheter insertion methods which are described above and below. Likewise, many of the features of the embodiments described may be used in various combinations with one another to create new embodiments, which are considered to be a part of this disclosure, as it would be too cumbersome to describe all of the numerous possible combinations and subcombinations of the disclosed features.

Following are a number of alternate embodiments of the perfusion filter catheter of the present invention illustrating additional features and variations in the configuration of the invention. In general, each of the described embodiments may be passively or actively deployed by the methods described above. Each embodiment of the perfusion filter catheter described can also be adapted for retrograde deployment via peripheral arterial access, such as femoral or subclavian artery access, or for antegrade or retrograde deployment via direct aortic puncture.

Figure 28:
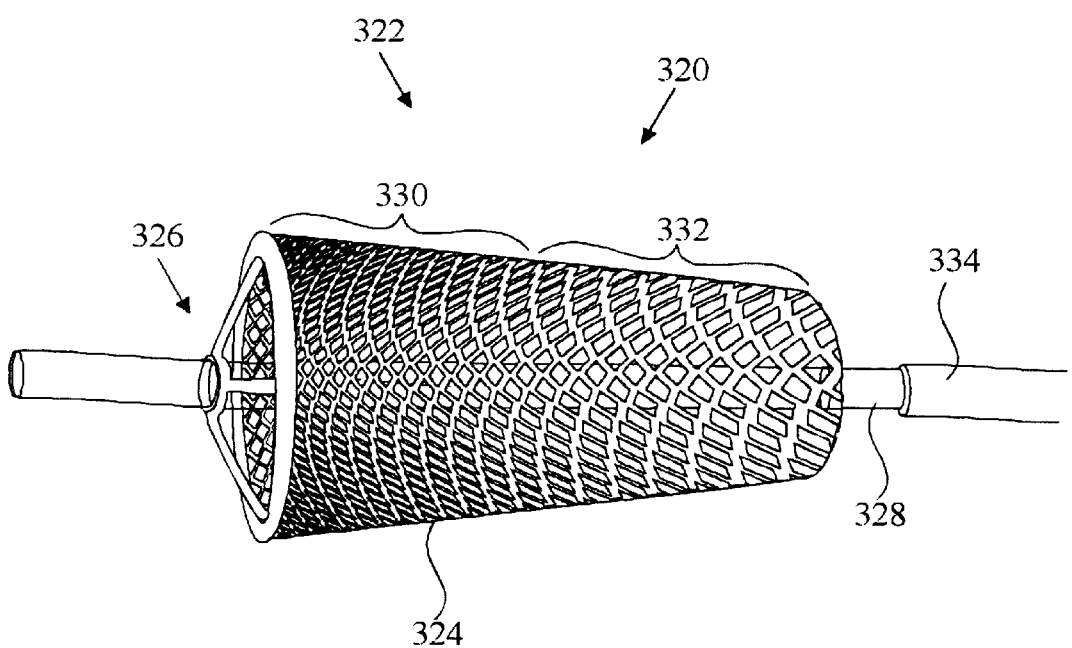
FIGS. 28 and 29 show a perfusion filter catheter having an embolic filter assembly with a graded porosity filter screen.
Figure 29:
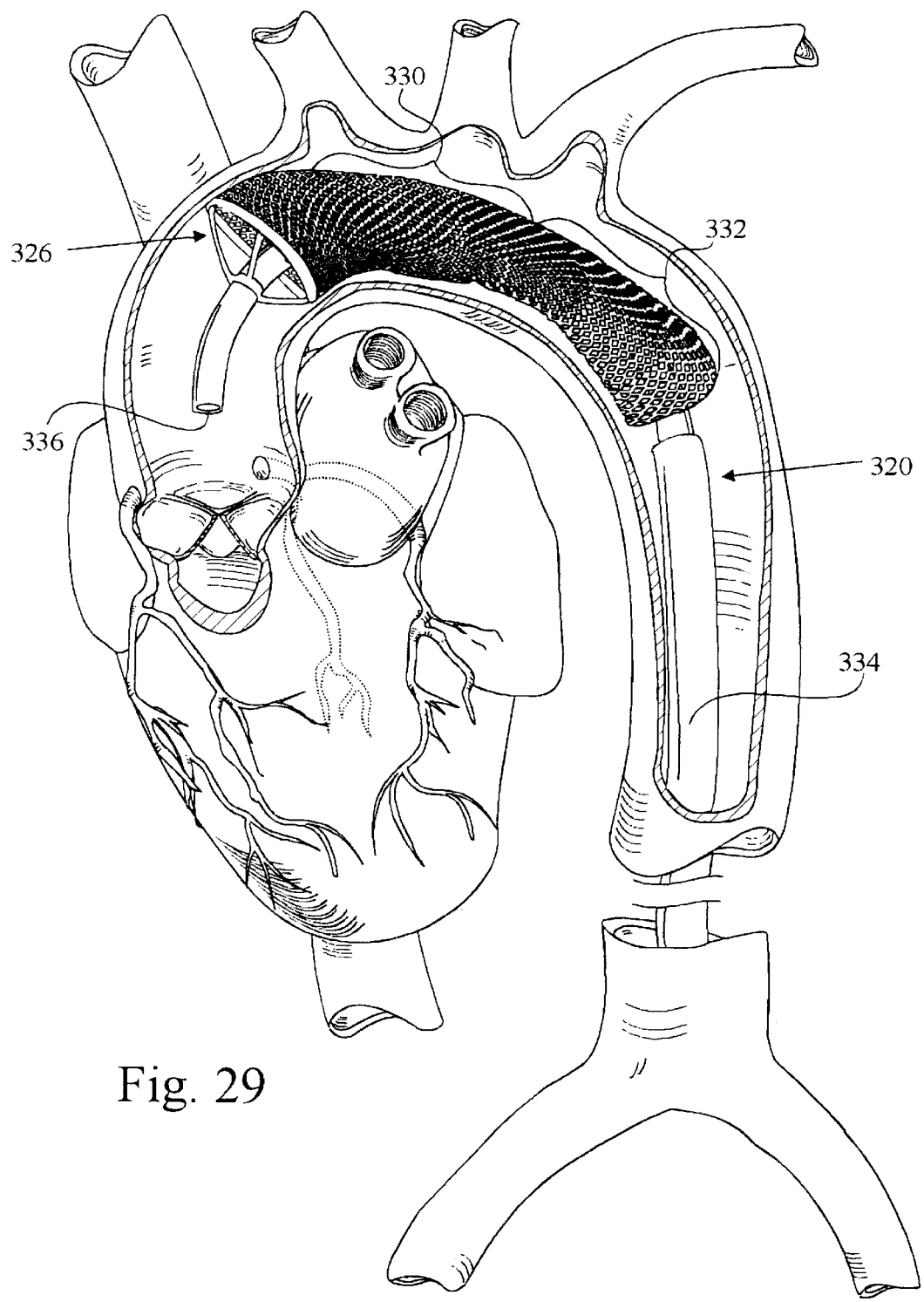

FIGS. 28 and 29 show a perfusion filter catheter 320 having an embolic filter assembly 322 with a graded porosity filter screen 324. The filter screen 324 is attached to a filter support structure 326 mounted on a catheter shaft 328 for antegrade or retrograde deployment. The filter screen 324 may be made in each of the configurations disclosed herein or any other convenient shape. By way of example, the filter screen 324 in this embodiment is depicted as being in the shape of a frustum of a cone. The filter screen 324 has an upstream end 330 and a downstream end 332. The upstream end 330 of the filter screen 324 has a finer filter mesh than the downstream end 332. Depending on the capabilities of the fabrication process used, the pore size of the filter screen 324 may make a gradual transition from the upstream end 330 to the downstream end 332 or there may be two or more discrete zones of varying pore size. In one preferred embodiment, the filter mesh on the upstream end 330 has a pore size of approximately 5–50 micrometers for capturing microemboli and macroemboli and the filter mesh on the downstream end 332 has a pore size of approximately 50–100 micrometers for capturing macroemboli only. The pore size of the filter screen 324 has been greatly exaggerated in FIG. 28 for clarity of illustration.

In use, the perfuision filter catheter 320 is introduced into the aorta with the embolic filter assembly 322 in a collapsed state within an outer tube 334, using one of the methods described above. The embolic filter assembly 322 is advanced across the aortic arch while in the collapsed state. When the upstream end 336 of the catheter 320 is positioned in the ascending aorta between the aortic valve and the brachiocephalic artery, the outer tube 334 is withdrawn and the embolic filter assembly 322 is either actively or passively deployed, as shown in FIG. 29. Preferably, the embolic filter assembly 292 is dimensioned so that when it is deployed, the upstream end 330 of the filter screen 324 is positioned in the vicinity of the ostia for the brachiocephalic artery and the left common carotid artery and the downstream end 332 of the filter screen 324 is positioned downstream of this position, preferably in the descending aorta. This configuration assures that all of the perfusate which is destined for the neurovasculature must pass through the finer, upstream end 330 of the filter screen 324 to remove all microemboli and macroemboli. Whereas, the perfusate which is destined for the viscera and the lower limbs, which are more tolerant of small emboli, need only pass through the downstream end 332 of the filter screen 324, so as to remove at least the macroemboli.

Figure 30:
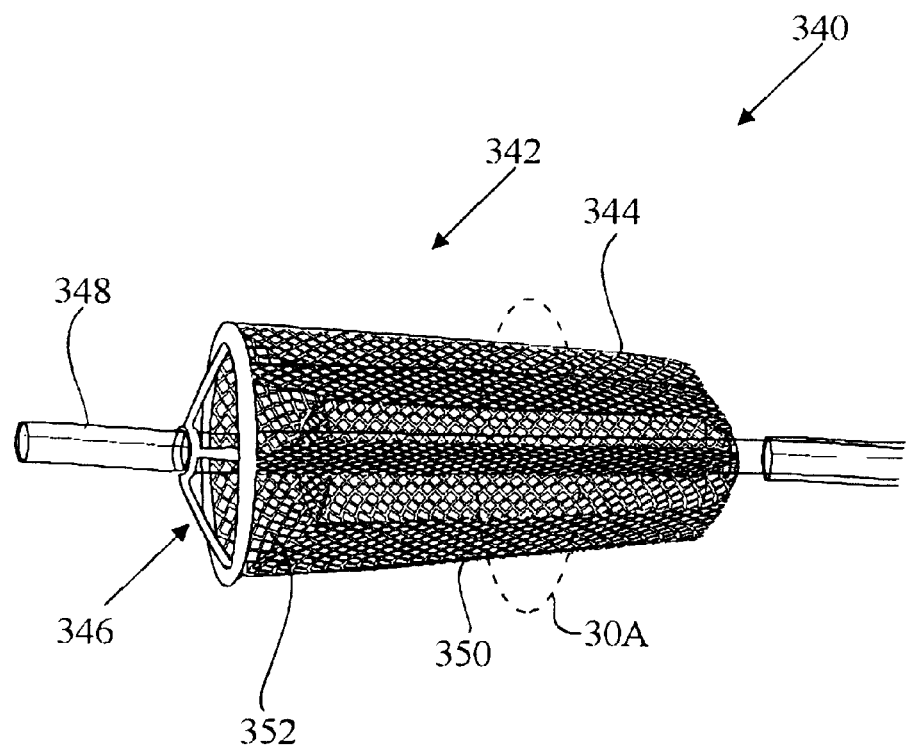
FIGS. 30 and 30A show a perfusion filter catheter having a longitudinally fluted embolic filter assembly.
Figure 30A:
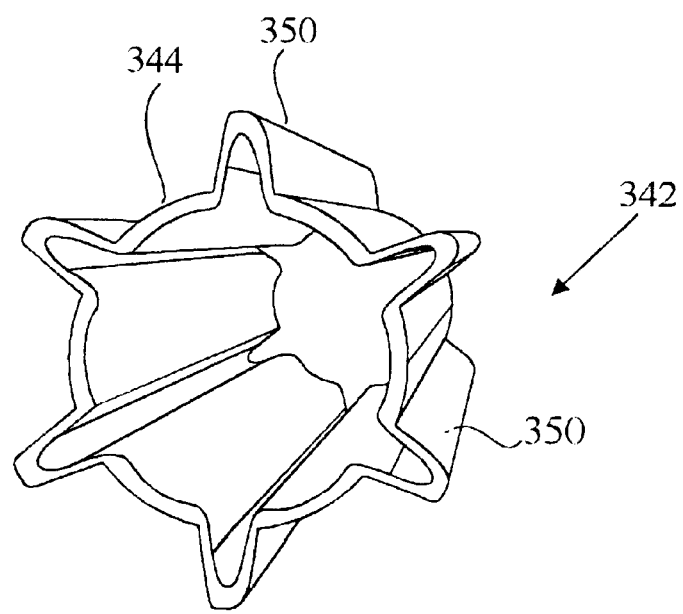

FIG. 30 shows a perfusion filter catheter 340 having a longitudinally fluted embolic filter assembly 342. The embolic filter assembly 342 has a filter screen 344 that is attached at its open distal end 352 to a filter support structure 346 mounted on a catheter shaft 348 for antegrade or retrograde deployment. The filter screen 344 has a plurality of longitudinally oriented folds or flutes 350. FIG. 30A is a cutaway section of the embolic filter assembly 342 cut along line 30A in FIG. 30 in order to better show the longitudinal flutes 350. The longitudinal flutes 350 provide additional surface area to the filter screen 344 to reduce pressure drop from blood flow across the embolic filter assembly 342. The longitudinal flutes 350 also serve to hold a majority of the filter screen 344 away from the aortic wall and away from the ostia of the arch vessels. The longitudinally fluted embolic filter assembly 342 can be adapted for passive or active deployment by any of the methods described above.

Figure 31:
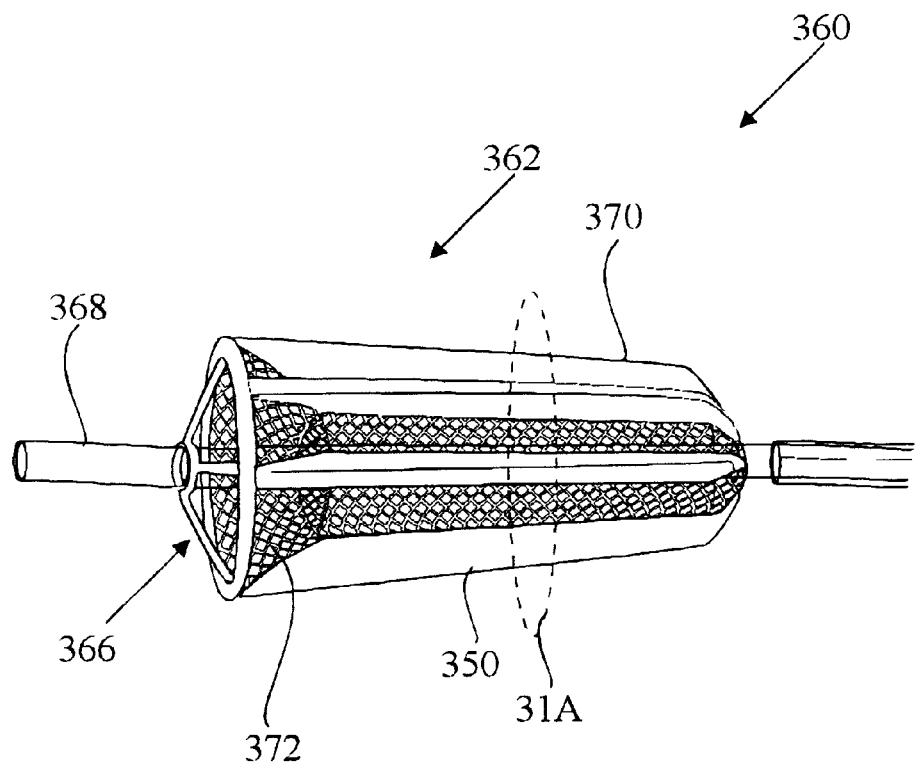
FIGS. 31 and 31A show a perfusion filter catheter having a longitudinally ribbed embolic filter assembly.
Figure 31A:
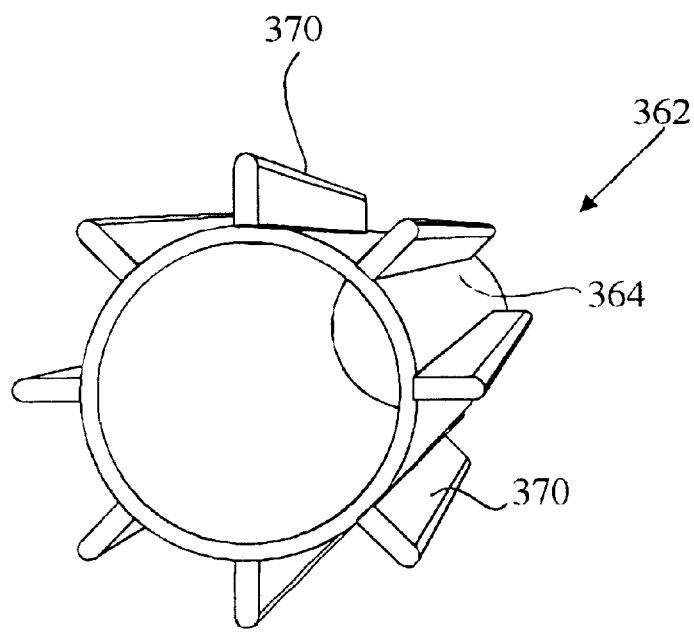

FIG. 31 shows a perfusion filter catheter 360 having a longitudinally ribbed embolic filter assembly 362. The embolic filter assembly 362 has a filter screen 364 that is attached at its open distal end 372 to a filter support structure 366 mounted on a catheter shaft 368 for antegrade or retrograde deployment. The filter screen 364 may be configured as a conical, trumpet, longitudinally fluted or other style of filter screen. The embolic filter assembly 362 has a plurality of longitudinally oriented ribs 370 positioned around the exterior of the filter screen 364. FIG. 31A is a cutaway section of the embolic filter assembly 362 cut along line 31A in FIG. 31 in order to better show the longitudinally oriented ribs 370. The longitudinal ribs 370 serve as standoff members to center the filter screen 364 within the aorta so as hold a majority of the filter screen 364 away from the aortic wall and away from the ostia of the arch vessels. The longitudinally ribbed embolic filter assembly 362 can be adapted for passive or active deployment by any of the methods described above.

Figure 32:
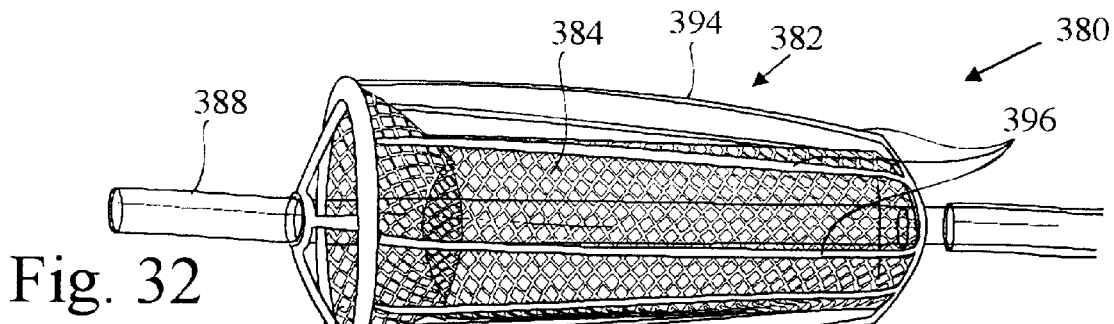
FIG. 32 shows a perfusion filter catheter having an embolic filter assembly that is surrounded by a cage of longitudinally oriented standoff members.

FIG. 32 shows a perfusion filter catheter 380 having an embolic filter assembly 382 that is surrounded by a cage 394 of standoff members 396. The embolic filter assembly 382 has a filter screen 384 that is attached at its open distal end 392 to a filter support structure 386 mounted on a catheter shaft 388 for antegrade or retrograde deployment. The filter screen 384 may be configured as a conical, trumpet, longitudinally fluted or other style of filter screen. The embolic filter assembly 382 further includes a plurality of standoff members 396 that form a cage 394 surrounding the filter screen 384. The standoff members 396 may be made of a resilient polymer or metal, such as an elastic or superelastic alloy, or a shape-memory material. The geometry of the standoff members 396 is quite variable. By way of example, FIG. 32 depicts the standoff members 396 as a plurality of longitudinally oriented wires which, together, form a roughly cylindrical cage 394. Other possible configurations include circumferential members, diagonal members, and combinations thereof. The standoff members 396 of the cage 394 serve to center the filter screen 384 within the aorta so as hold a majority of the filter screen 384 away from the aortic wall and away from the ostia of the arch vessels. The embolic filter assembly 382 and the standoff members 396 of the cage 394 can be adapted for passive or active deployment by any of the methods described above.

Figure 33:
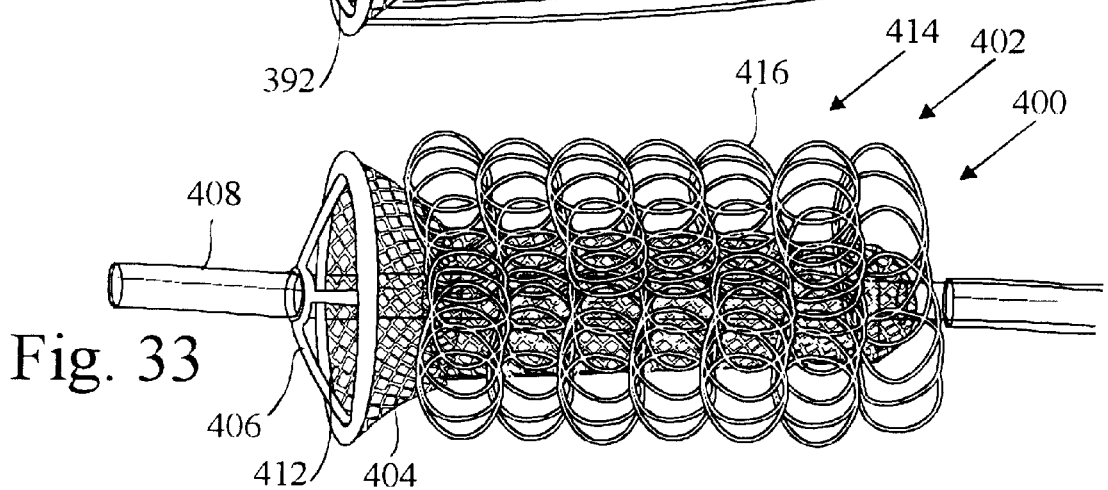
FIG. 33 shows a perfusion filter catheter having an embolic filter assembly that is surrounded by a cage of coiled wire standoff members.

FIG. 33 shows a perfusion filter catheter 400 having an embolic filter assembly 402 that is surrounded by a cage 414 of coiled wire standoff members 416. The embolic filter assembly 402 has a filter screen 404 that is attached at its open distal end 412 to a filter support structure 406 mounted on a catheter shaft 408 for antegrade or retrograde deployment. The filter screen 404 may be configured as a conical, trumpet, longitudinally fluted or other style of filter screen. The embolic filter assembly 402 further includes a plurality of loosely coiled wire standoff members 416 which form a cage 414 surrounding the filter screen 404. The coiled standoff members 416 may be made of a resilient polymer or metal, such as an elastic or superelastic alloy, or a shape-memory material. The coiled standoff members 416 of the cage 414 serve to center the filter screen 404 within the aorta so as hold a majority of the filter screen 404 away from the aortic wall and away from the ostia of the arch vessels. The embolic filter assembly 402 and the standoff members 416 of the cage 414 can be adapted for passive or active deployment by any of the methods described above.

Figure 34:
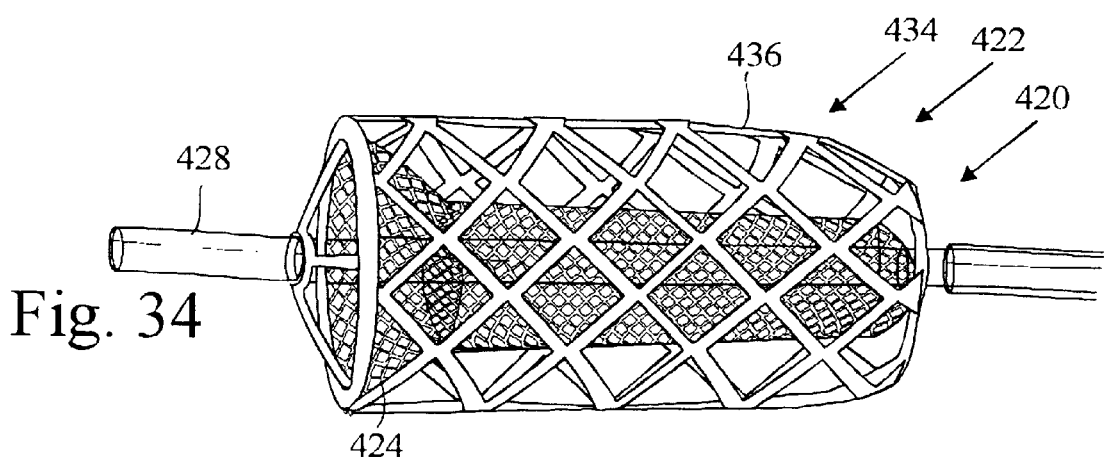
FIG. 34 shows a perfusion filter catheter having an embolic filter assembly that is surrounded by a cage of coarse netting.

FIG. 34 shows a perfusion filter catheter 420 having an embolic filter assembly 422 that is surrounded by a cage 434 of coarse netting 436. The embolic filter assembly 422 has a filter screen 424 that is attached at its open distal end 432 to a filter support structure 426 mounted on a catheter shaft 428 for antegrade or retrograde deployment. The filter screen 424 may be configured as a conical, trumpet, longitudinally fluted or other style of filter screen. The embolic filter assembly 422 further includes a coarse netting 436, which forms a roughly cylindrical cage 434 surrounding the filter screen 424. The netting 436 may be made of a resilient polymer or metal, such as an elastic or superelastic alloy, or a shape-memory material. The netting 436 of the cage 434 serves to center the filter screen 424 within the aorta so as hold a majority of the filter screen 424 away from the aortic wall and away from the ostia of the arch vessels. The embolic filter assembly 422 and the coarse netting 436 of the cage 434 can be adapted for passive or active deployment by any of the methods described above.

Figure 35:
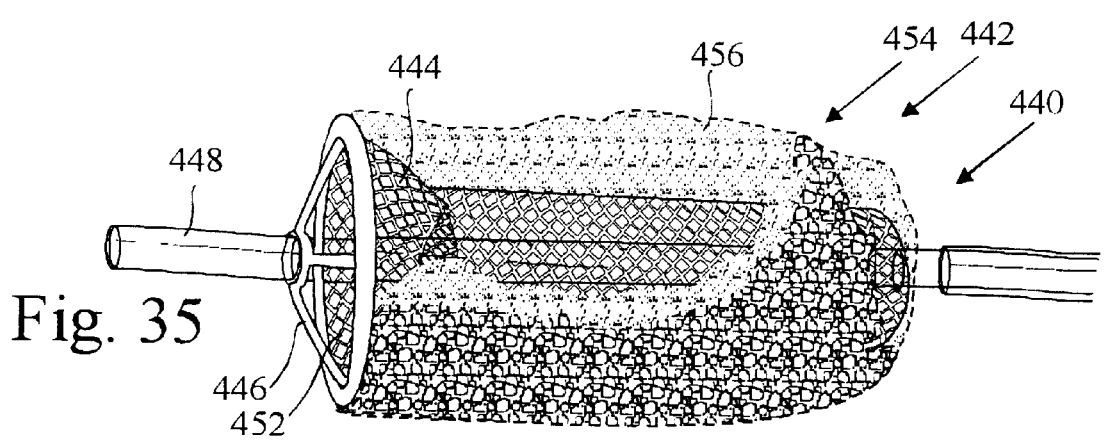
FIG. 35 shows a cutaway view of a perfusion filter catheter having an embolic filter assembly that is surrounded by a fender made from a porous foam or a fibrous network.

FIG. 35 shows a cutaway view of a perfusion filter catheter 440 having an embolic filter assembly 442 that is surrounded by a fender 454 made from a porous foam or a fibrous network 456. The embolic filter assembly 442 has a filter screen 444 that is attached at its open distal end 452 to a filter support structure 446 mounted on a catheter shaft 448 for antegrade or retrograde deployment. The filter screen 444 may be configured as a conical, trumpet, longitudinally fluted or other style of filter screen. The embolic filter assembly 442 further includes a roughly cylindrical fender 454 made from a highly porous foam or a fibrous network 456, which surrounds the filter screen 444. The fender 454 may be made of a highly porous open cell polymer foam or a network of polymeric fibers. The fender 454 serves to center the filter screen 444 within the aorta so as hold a majority of the filter screen 444 away from the aortic wall and away from the ostia of the arch vessels. The embolic filter assembly 442 and the fender 454 can be adapted for passive or active deployment or a combination thereof.

Figure 36:
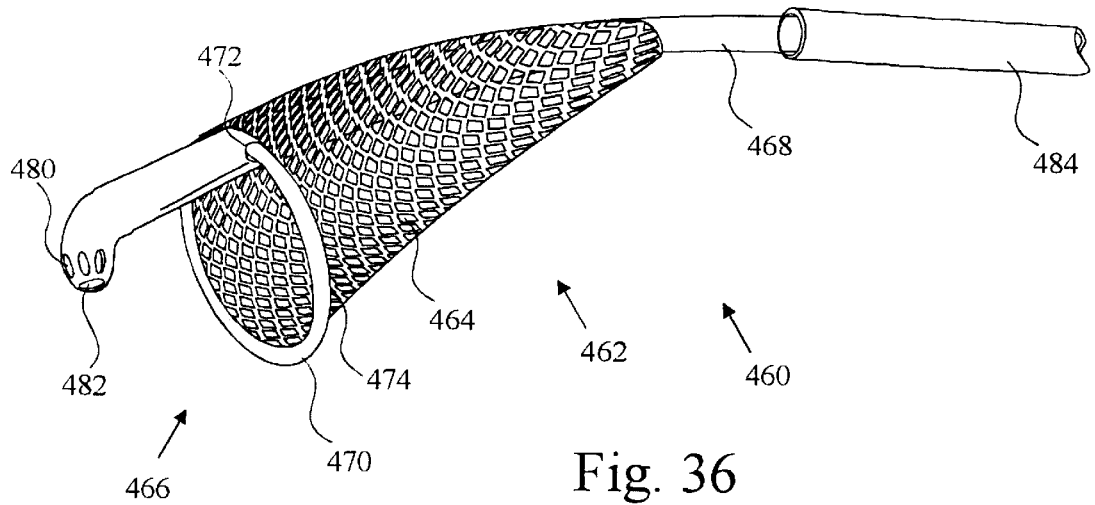
FIGS. 36 and 37 show an alternate embodiment of a perfusion filter catheter with a passively deployed embolic filter assembly.
Figure 37:
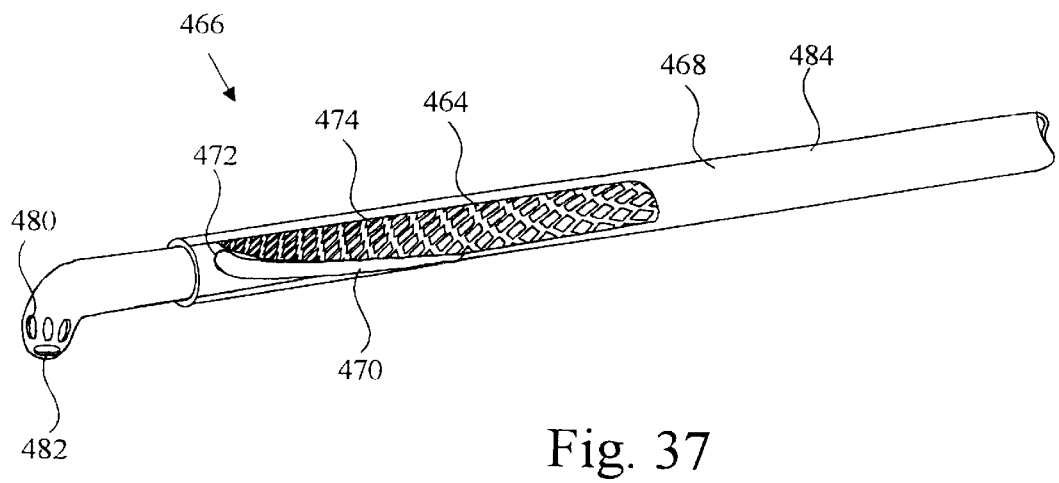

FIGS. 36 and 37 show an alternate embodiment of a perfusion filter catheter 460 with a passively deployed embolic filter assembly 462. The embolic filter assembly 462 has a filter screen 464 that is attached at its open distal end 474 to a filter support structure 466 mounted on a catheter shaft 468 for antegrade or retrograde deployment. The proximal end 476 of the filter screen 464 is sealingly attached to the catheter shaft 468. The filter screen 464 may be configured as a conical, trumpet or other style of filter screen. The filter support structure 466 has an outer hoop 470 which is attached by a perpendicular leg 472 to the catheter shaft 468. Preferably, the outer hoop 470 is made of a resilient polymer or metal, such as an elastic or superelastic alloy, or possibly a shape-memory material. The filter support structure 466, in this embodiment, has no struts. Optionally, the distal end 478 of the catheter shaft 468 may be curved toward the center of the outer hoop 470 to help center the perfusion port 480 located at the distal end of the catheter shaft 468 within the aorta when the catheter 460 is deployed. Also, the perfusion port 480 may optionally include additional side ports or a flow diffuser, as shown, to reduce jetting when oxygenated blood is infused through the perfusion lumen 482.

The perfusion filter catheter 460 is prepared for use by bending the outer hoop 470 in the proximal direction or wrapping it around the catheter shaft 468, then folding or wrapping the material of the filter screen 464 around the catheter shaft 468. An outer tube 484 is placed over the embolic filter assembly 462 to hold it in the collapsed position, as shown in FIG. 37. The catheter 460 is introduced and the embolic filter assembly 462 is advanced across the aortic arch while in the collapsed state. When the distal end 474 of the embolic filter assembly 462 is positioned in the ascending aorta between the aortic valve and the brachiocephalic artery, the outer tube 484 is withdrawn and the resilient outer hoop 470 expands to deploy the embolic filter assembly 462, as shown in FIG. 36. The outer hoop 470 and the distal end 474 of the filter screen 464 will seal against the aortic wall. After use, the embolic filter assembly 462 is returned to the collapsed position by advancing the outer tube 484 distally over the filter screen 464 and the filter support structure 466, then the catheter 460 is withdrawn from the patient.

FIGS. 38–41 show an alternate embodiment of a perfusion filter catheter 490 with an actively deployed embolic filter assembly 492. The embolic filter assembly 492 has a filter screen 494 with a sewn tubular channel 496 which extends circumferentially around the open distal end 498 of the filter screen 494. The distal end 498 of the filter screen 494 is attached on one side to the catheter shaft 504, and the proximal end 506 of the filter screen 494 is sealingly attached to the catheter shaft 504. The filter screen 494 may be configured as a conical, trumpet or other style of filter screen. The filter support structure in this embodiment consists of a preshaped, superelastic actuation wire 500, which, when the embolic filter assembly 492 is in the collapsed state, resides in a second lumen 502 within the catheter shaft 504. Preferably, the actuation wire 500 has a bead or small loop 508 at its distal end to create a blunt, non-piercing tip. The second lumen 502 of the catheter shaft 504 communicates with the tubular channel 496 at the distal end 498 of the filter screen 494. When the actuation wire 500 is extended, it forms a hoop as it passes through the tubular channel 496 of the filter screen 494.

Optionally, the distal end 510 of the catheter shaft 504 may be curved toward the center of the embolic filter assembly 492 to help center the perfusion port 510 located at the distal end of the catheter shaft 504 within the aorta when the catheter 490 is deployed. Also, the perfusion port 510 may optionally include additional side ports or a flow diffuser, as shown, to reduce jetting when oxygenated blood is infused through the perfusion lumen 512 during cardiopulmonary bypass.

Figure 38:
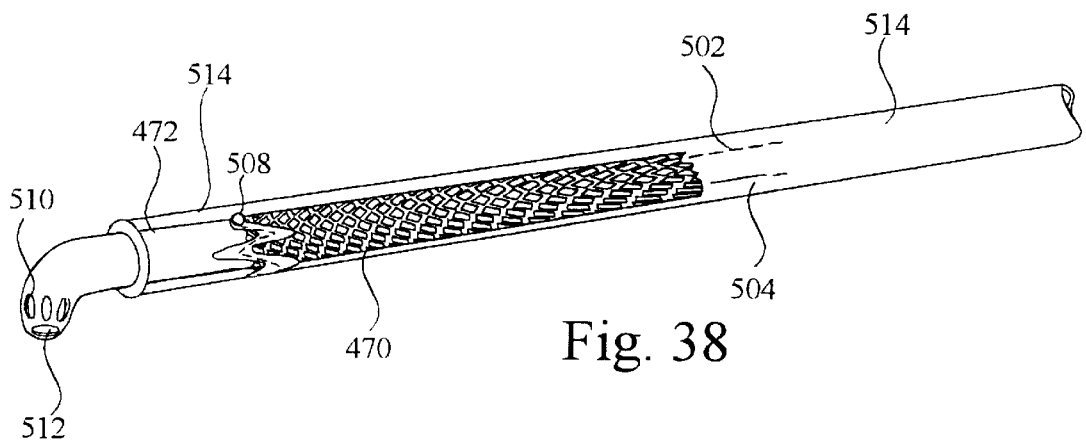
FIGS. 38–41 show an alternate embodiment of a perfusion filter catheter with an actively deployed embolic filter assembly having a filter support structure with a preshaped, superelastic actuation wire.
Figure 39:
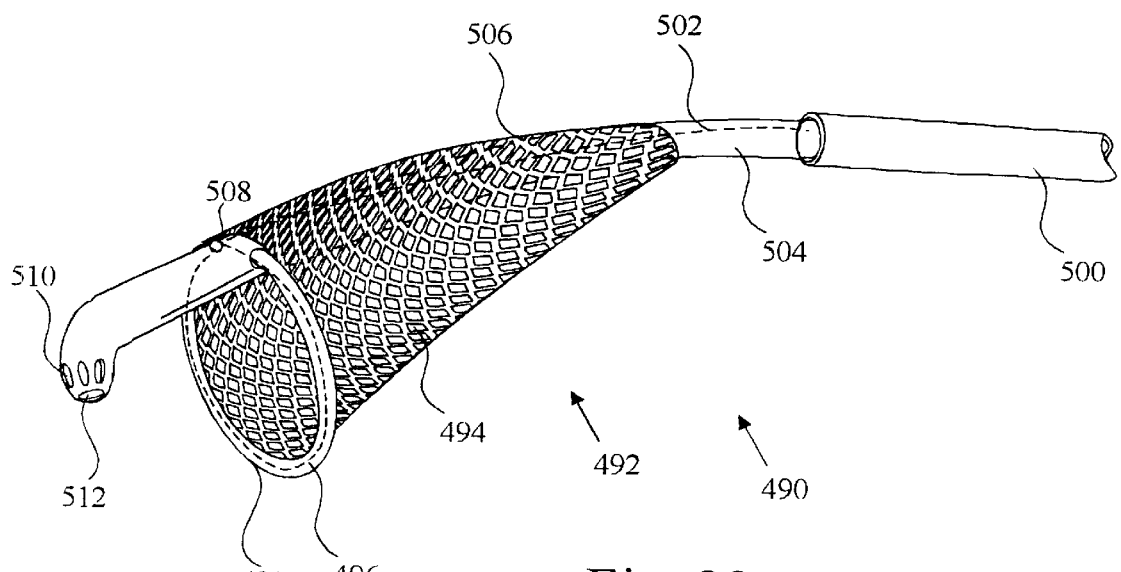

The perfusion filter catheter 490 is prepared for use by withdrawing the actuation wire 500 into the second lumen 502, then folding or wrapping the flexible material of the filter screen 494 around the catheter shaft 504. Optionally, an outer tube 514 may be placed over the embolic filter assembly 492 to hold it in the collapsed position, as shown in FIG. 38. The catheter 490 is introduced and the embolic filter assembly 492 is advanced across the aortic arch while in the collapsed state. When the distal end 498 of the embolic filter assembly 492 is positioned in the ascending aorta between the aortic valve and the brachiocephalic artery, the outer tube 514 is withdrawn, which allows the filter screen 494 to unwrap from the catheter shaft 504, as shown in FIG. 39.

Figure 40:
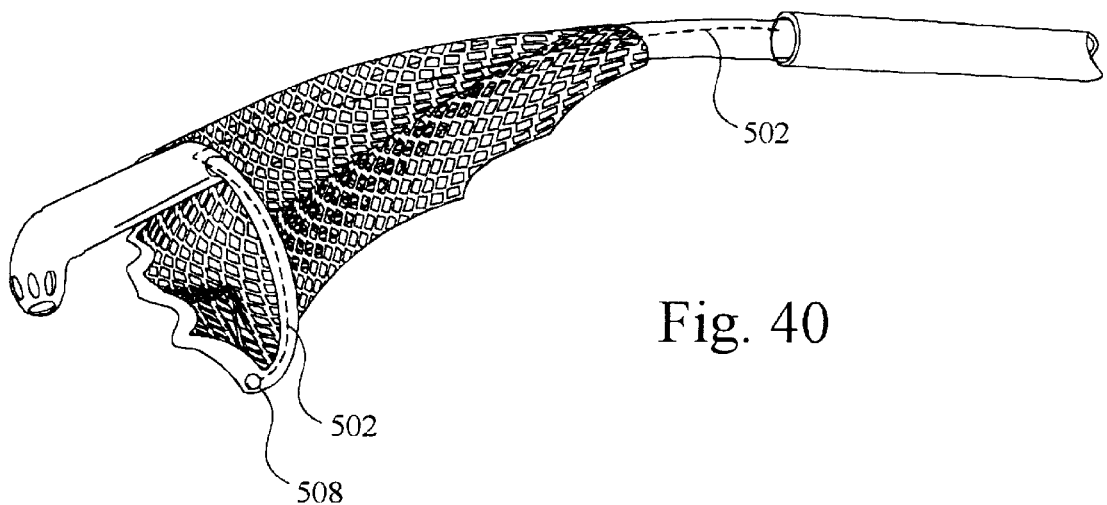
Figure 41:
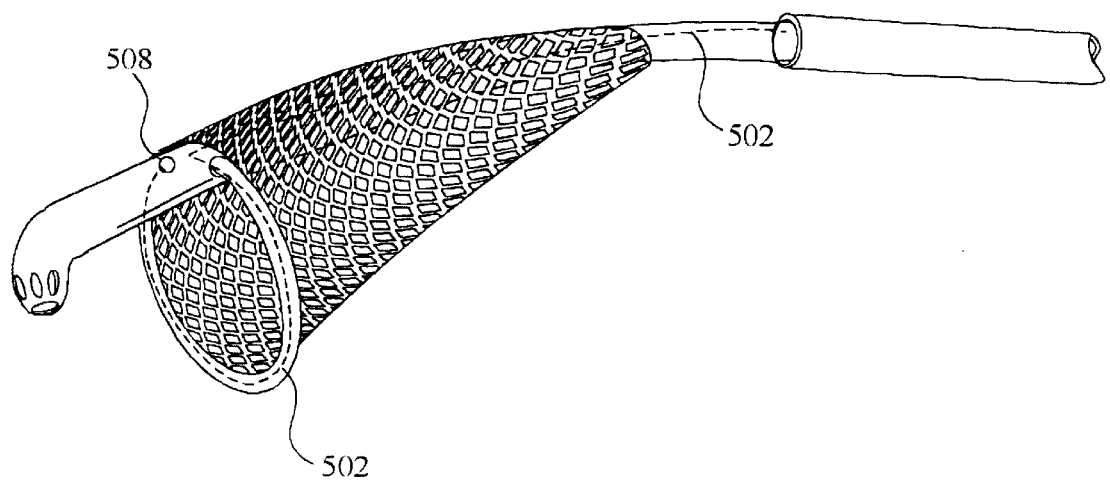

Then, the preshaped, superelastic actuation wire 500 is advanced distally so that it begins to form a hoop as it passes through the tubular channel 496 at the distal end 498 of the filter screen 494, as shown in FIG. 40. The actuation wire 500 is further advanced until it forms a complete hoop, as shown in FIG. 41, thereby sealing the distal end 498 of the filter screen 494 against the aortic wall. After use, the embolic filter assembly 492 is returned to the collapsed position as described above, then the catheter 490 is withdrawn from the patient.

Figure 42:
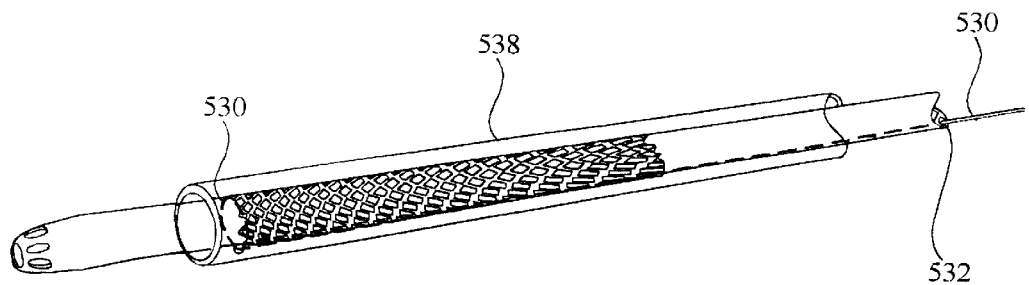
FIGS. 42 and 43 show another alternate embodiment of a perfusion filter catheter with an actively deployed embolic filter assembly having a filter support structure with a preshaped, superelastic wire purse string loop.
Figure 43:
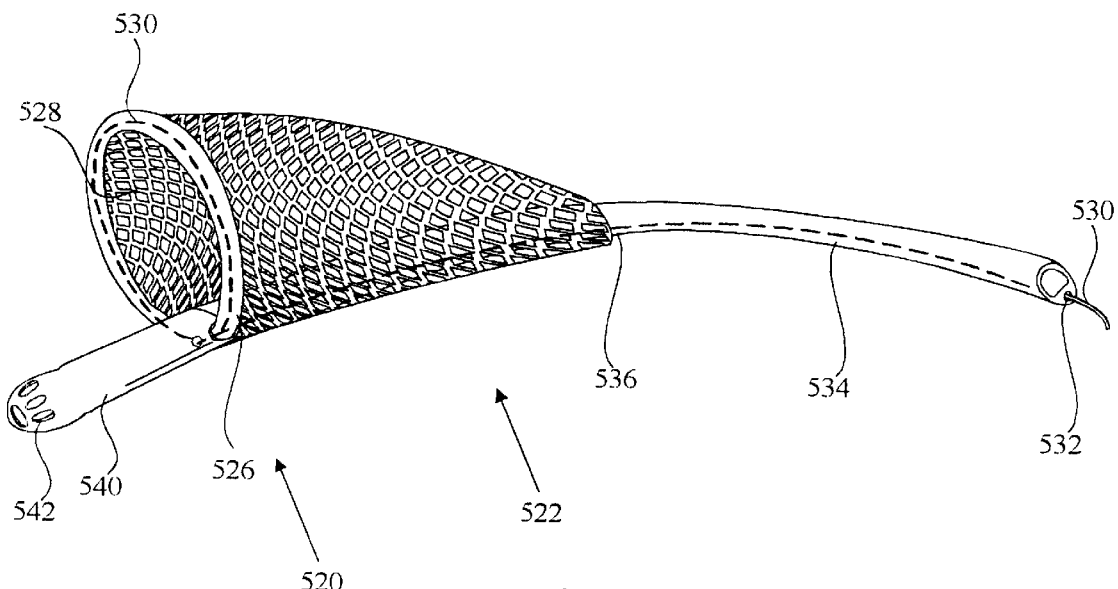

FIGS. 42 and 43 show another alternate embodiment of a perfusion filter catheter 520 with an actively deployed embolic filter assembly 522. The embolic filter assembly 522 has a filter screen 524 with a sewn tubular channel 526 which extends circumferentially around the open distal end 528 of the filter screen 524. The distal end 528 of the filter screen 524 is attached on one side to the catheter shaft 534, and the proximal end 536 of the filter screen 524 is sealingly attached to the catheter shaft 534. The filter screen 524 may be configured as a conical, trumpet or other style of filter screen. The filter support structure in this embodiment consists of a preshaped, elastic or superelastic wire loop 530. The wire loop 530 passes through the tubular channel 526 at the distal end 528 of the filter screen 524. When the embolic filter assembly 522 is in the collapsed position, the wire loop 530 is withdrawn into a second lumen 532 within the catheter shaft 534, as shown in FIG. 42. In the collapsed position, the wire loop 530 acts as a purse string to close the filter screen 524 tightly around the catheter shaft 534. When the wire loop 530 is advanced distally, it forms a hoop that holds the distal end 528 of the filter screen 524 open, as shown in FIG. 43.

Optionally, the distal end 540 of the catheter shaft 534 may be curved toward the center of the embolic filter assembly 522 to help center the perfusion port 542 located at the distal end of the catheter shaft 534 within the aorta when the catheter 520 is deployed. Also, the perfusion port 540 may optionally include additional side ports or a flow diffuser, as shown, to reduce jetting when oxygenated blood is infused through the perfusion lumen 544 during cardiopulmonary bypass.

The perfusion filter catheter 520 is prepared for use by withdrawing the wire loop 530 into the second lumen 532, then folding or wrapping the flexible material of the filter screen 524 around the catheter shaft 534. Optionally, an outer tube 538 may be placed over the embolic filter assembly 522 to hold it in the collapsed position. The catheter 520 is introduced and the embolic filter assembly 522 is advanced across the aortic arch while in the collapsed state. When the distal end 528 of the embolic filter assembly 522 is positioned in the ascending aorta between the aortic valve and the brachiocephalic artery, the outer tube 538 is withdrawn, and the preshaped, superelastic wire loop 530 is advanced distally so that it forms a hoop that holds the distal end 528 of the filter screen 524 open and seals against the aortic wall. The inherent adjustability of the wire loop 530 used to deploy the embolic filter assembly 522 naturally compensates for patient-to-patient variations in aortic luminal diameter. After use, the embolic filter assembly 522 is returned to the collapsed position by withdrawing the wire loop 530 into the second lumen 532. This closes the filter screen 524 like a purse string to capture any potential emboli that are in the embolic filter assembly 522. Then, the catheter 520 is withdrawn from the patient.

Figure 44:
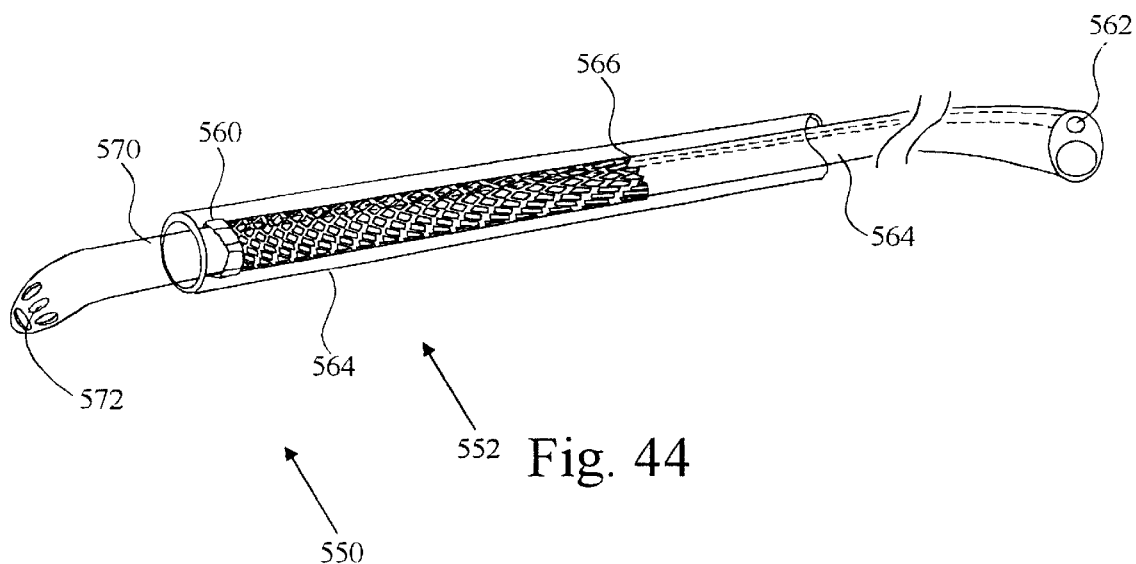
FIGS. 44 and 45 show another alternate embodiment of a perfusion filter catheter with an actively deployed inflatable embolic filter assembly.
Figure 45:
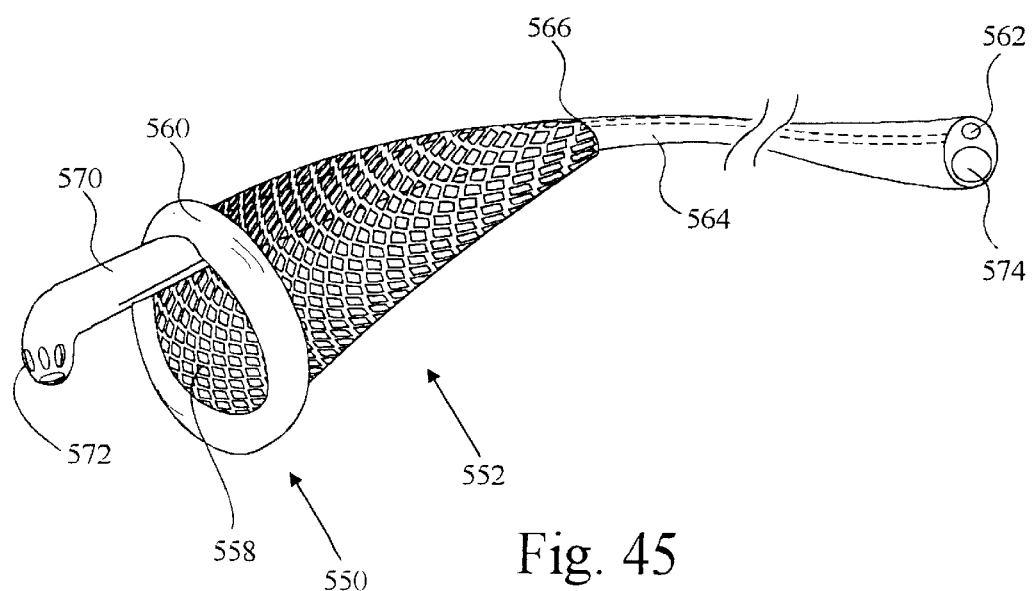

FIGS. 44 and 45 show another alternate embodiment of a perfusion filter catheter 550 with an actively deployed embolic filter assembly 552. The embolic filter assembly 552 has a filter screen 554 with an open distal end 558 that is attached to a toroidal balloon 560. The toroidal balloon 560 is attached on one side to the catheter shaft 564 and it is fluidly connected to an inflation lumen 562 within the catheter shaft 564. The proximal end 566 of the filter screen 554 is sealingly attached to the catheter shaft 564. The filter screen 554 may be configured as a conical, trumpet or other style of filter screen. Optionally, the distal end 570 of the catheter shaft 564 may be curved toward the center of the embolic filter assembly 552 to help center the perfusion port 572 located at the distal end of the catheter shaft 564 within the aorta when the catheter 550 is deployed. Also, the perfusion port 570 may optionally include additional side ports or a flow diffuser, as shown, to reduce jetting when oxygenated blood is infused through the perfusion lumen 574 during cardiopulmonary bypass.

The perfusion filter catheter 550 is prepared for use by deflating the toroidal balloon 560, then folding or wrapping the deflated toroidal balloon 560 and the filter screen 554 around the catheter shaft 564. Optionally, an outer tube 564 may be placed over the embolic filter assembly 552 to hold it in the collapsed position, as shown in FIG. 44. The catheter 550 is introduced and the embolic filter assembly 552 is advanced across the aortic arch while in the collapsed state. When the distal end 558 of the embolic filter assembly 552 is positioned in the ascending aorta between the aortic valve and the brachiocephalic artery, the outer tube 564 is pulled back to expose the embolic filter assembly 552. Then, the embolic filter assembly 202 is deployed by inflating the toroidal balloon 560 with fluid injected through the inflation lumen 562, as shown in FIG. 45. When the embolic filter assembly 552 is deployed, the toroidal balloon 560 seals against the inner wall of the aorta. Preferably, at least the outer wall of the toroidal balloon 560 is somewhat compliant when inflated in order to compensate for patient-to-patient variations in aortic luminal diameter. After use, the toroidal balloon 560 is deflated and the catheter 550 is withdrawn from the patient.

Ideally, it is preferable that the embolic filter assembly of the perfusion filter catheter be deployed continuously throughout the entire period of cardiopulmonary bypass or extracorporeal perfusion. It is most critical, however, that the embolic filter assembly be deployed during periods when the potential for embolization is the highest, such as during manipulations of the heart and the aorta, during clamping and unclamping of the aorta and during the initial period after the heart is restarted following cardioplegic arrest. It has been previously stated that, for continuous deployment of a filter device in the aortic lumen, it is desirable for the filter mesh to have a surface area of 3–10 in$^2$. The shallow, cone-shaped aortic filter devices illustrated in the known prior art only manage to provide surface areas at the lower end of this desired range in the largest of human aortas (approximately 3.0–3.9 in$^2$ in aortas of 3.5–4.0 cm diameter estimated based on the drawings and descriptions in the prior art disclosures) and in no cases are there embodiments disclosed which could provide surface areas in the middle and upper end of this range or that could even meet the minimum limit of this desired range in more typically sized aortas in the range of 2.5–3.5 cm diameter. Consequently, it is the opinion of the present inventors that the prior art does not provide an adequate solution to the technical problem that it illuminates.

The solution to this dilemma is to provide a filter assembly that has a greater ratio of filter surface area to the cross-sectional area of the aortic lumen. (The cross-sectional area of the aortic lumen being approximately equal to the area of the open upstream end of the embolic filter assembly at its deployed diameter within the aorta.) Preferably, the embolic filter assembly should provide a ratio of the filter surface area to the cross-sectional area of the aortic lumen of greater than approximately 2, more preferably greater than 3, more preferably greater than 4, more preferably greater than 5 and most preferably greater than 6. With these ratios of the filter surface area to the cross-sectional area of the aortic lumen, it is possible to achieve a filter mesh surface area of 3–10 in$^2$ or greater in all typical adult human aortas ranging from 2.0 to 4.0 cm in diameter. Furthermore, given the embolic filter assembly structures that have been disclosed herein, it is envisioned that ratios of the filter surface area to the cross-sectional area of the aortic lumen of 8, 10, 12 and even greater are readily achievable. Higher ratios such as these are desirable as they allow a very fine filter mesh to be utilized to effectively capture both macroemboli and microemboli without compromising the aortic blood flow. Along with this, it is preferable to utilize an embolic filter assembly structure or other means that maximizes the effective surface area of the filter mesh by holding at least a majority of the filter mesh away from the aortic wall or any other structures that might potentially obstruct flow through the filter mesh.

To further illustrate this point, the following are given as examples of embolic filter assemblies exhibiting the desired range of ratios of the filter surface area to the cross-sectional area of the aortic lumen. These examples are merely illustrative of some of the possible embodiments of the embolic filter assembly and should not be interpreted as limiting in any way to the scope of the present invention. Turning first to FIGS. 1–3, there is illustrated an embolic filter assembly that is approximately conical in shape. In order to achieve a ratio of the filter surface area to the cross-sectional area of the aortic lumen of greater than approximately 2, a conical filter assembly must have a filter length L of greater than the aortic diameter D. To achieve a ratio of the filter surface area to the cross-sectional area of the aortic lumen of greater than approximately 4, a conical filter assembly must have a filter length L of greater than twice the aortic diameter D. To achieve a ratio of the filter surface area to the cross-sectional area of the aortic lumen of greater than approximately 6, a conical filter assembly must have a filter length L of greater than three times the aortic diameter D. With these ratios of the filter surface area to the cross-sectional area of the aortic lumen, it is possible to achieve a filter mesh surface area of 3–10 in$^2$ or greater in all typical adult human aortas ranging from 2.0 to 4.0 cm in diameter. Greater length to diameter ratios will provide more improved ratios of the filter surface area to the cross-sectional area of the aortic lumen.

Turning next to FIGS. 7–8, 15–17 and 25–27, there are illustrated embolic filter assemblies having an approximately trumpet-shaped geometry that includes an approximately conical upstream section connected to an approximately cylindrical extension with a closed downstream end. This geometry provides an improvement in the ratio of the filter surface area to the cross-sectional area of the aortic lumen of approximately 15 to 50 percent compared with the simple conical geometry. Thus, even greater ratios of the filter surface area to the cross-sectional area of the aortic lumen are readily achieved using this trumpet-shaped geometry. Further improvements of the ratio of the filter surface area to the cross-sectional area of the aortic lumen can be realized with the convoluted embolic filter assemblies illustrated in FIGS. 18–20, 20–23 and 30. With these convoluted geometries, ratios of the filter surface area to the cross-sectional area of the aortic lumen of 2–12 or even greater can be achieved.

Each of the embodiments of the invention described herein may be used for administration of standard cardiopulmonary bypass and cardioplegic arrest by combining the aortic filter catheter with a standard aortic crossclamp and a standard arterial perfusion cannula inserted into the ascending aorta between the crossclamp and the embolic filter assembly. Where the aortic filter catheter includes an integral perfusion lumen, the CPB system can be simplified by the eliminating the separate arterial perfusion cannula. The CPB system can be further simplified by incorporating an aortic occlusion device into the aortic filter catheter and eliminating the aortic crossclamp. Such a system would allow percutaneous transluminal administration of cardiopulmonary bypass and cardioplegic arrest with protection from undesirable embolic events.

FIGS. 46–50 show the operation of an embodiment of a perfusion filter catheter 600 that combines an embolic filter assembly 602 with a toroidal balloon aortic occlusion device 604. The embolic filter assembly 602 and the toroidal balloon aortic occlusion device 604 are mounted on an elongated catheter shaft 606 that may be adapted for peripheral introduction via the femoral artery or subclavian artery or for central insertion directly into the ascending aorta. The toroidal balloon aortic occlusion device 604 is connected to an inflation lumen within the elongated catheter shaft 606. A cardioplegia lumen, which may also serve as a guidewire lumen, connects to a cardioplegia port 608 at the distal end of the catheter shaft 606. A perfusion lumen connects to one or more perfusion ports 610 located on the catheter shaft 606 downstream from the toroidal balloon aortic occlusion device 604, but upstream of the embolic filter assembly 602.

Figure 46:
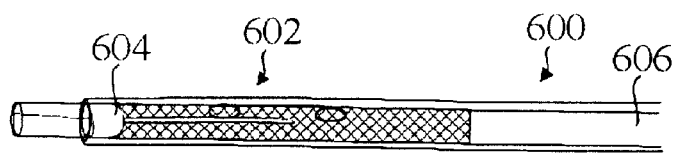
FIGS. 46–50 show the operation of an embodiment of a perfusion filter catheter that combines an embolic filter assembly with a toroidal balloon aortic occlusion device.
Figure 47:
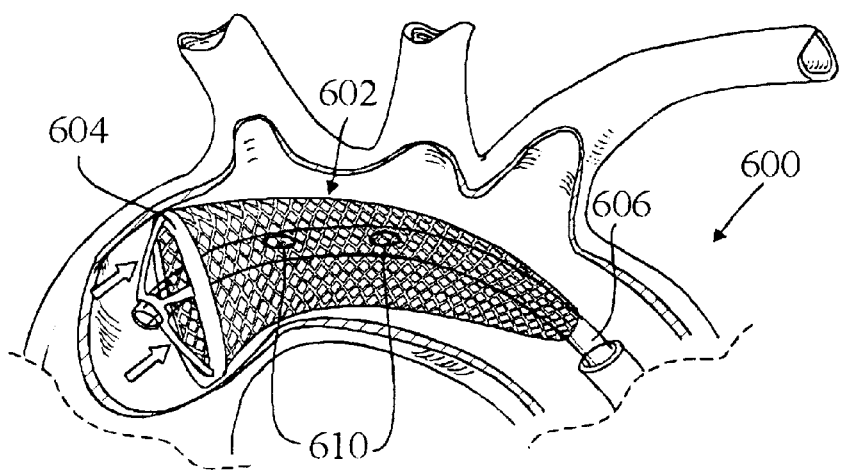

FIG. 46 shows the perfusion filter catheter 600 in the collapsed or undeployed state with the embolic filter assembly 602 and the toroidal balloon aortic occlusion device 604 collapsed or folded about the elongated catheter shaft 606. The perfuision filter catheter 600 is inserted in the collapsed state and advanced into the patient's ascending aorta until the embolic filter assembly 602 is positioned between the coronary ostia and the brachiocephalic artery. The toroidal balloon aortic occlusion device 604 is then inflated to expand and deploy the embolic filter assembly 602, as shown in FIG. 47. The embolic filter assembly 602 may assume a simple conical shape or, more preferably, one of the surface area increasing geometries described above. In addition, the embolic filter assembly 602 may include a structure or other means to hold the filter material apart from the aortic wall to maximize the effective filter area. With the embolic filter assembly 602 deployed, cardiopulmonary bypass with embolic protection can be started through the perfusion ports 610.

Figure 48:
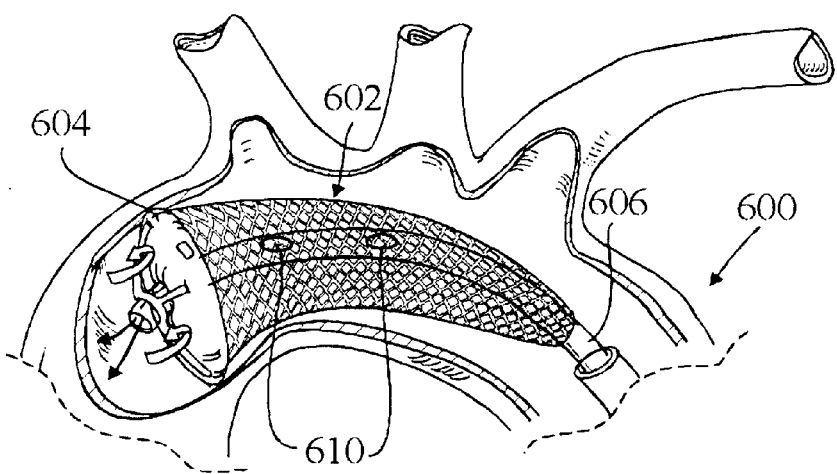
Figure 49:
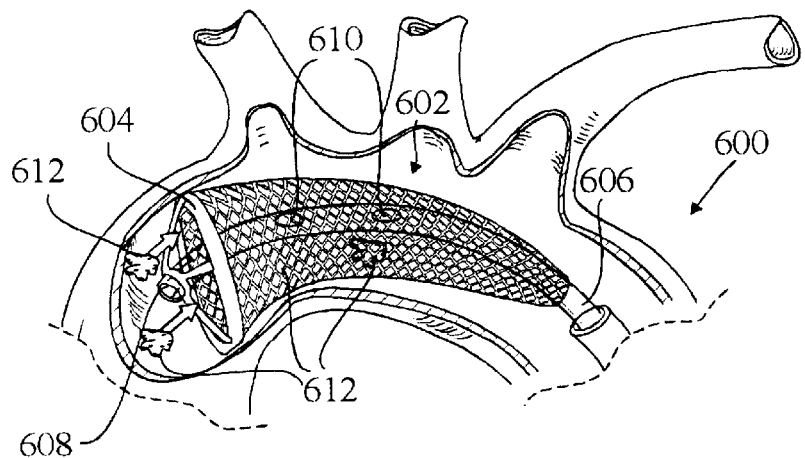
Figure 50:
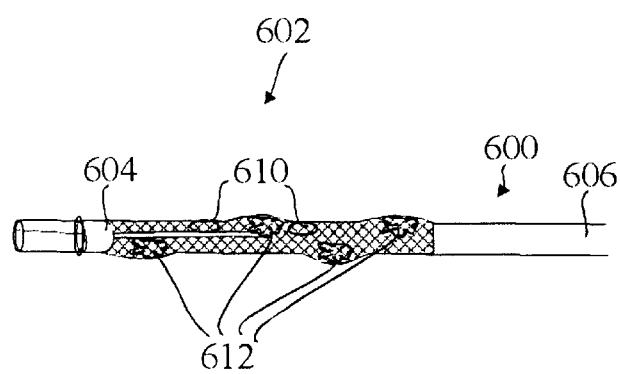

When it is desired to initiate cardioplegic arrest, the toroidal balloon aortic occlusion device 604 is further inflated until it expands inward to occlude the aortic lumen, as shown in FIG. 48. A cardioplegic agent is infused through the cardioplegia port 608 and into the coronary arteries to arrest the heart. Oxygenated blood continues to be infused through the perfusion ports 610. After completion of the surgical procedure, the toroidal balloon aortic occlusion device 604 is partially deflated, leaving the embolic filter assembly 602 deployed, as shown in FIG. 49. Oxygenated blood enters the coronary arteries to restart the heart beating. If any embolic materials 612 are dislodged during manipulation of the heart or when the heart resumes beating, they will be captured by the embolic filter assembly 602. Once the patient is weaned off of bypass, the toroidal balloon aortic occlusion device 604 is deflated to collapse the embolic filter assembly 602, as shown in FIG. 50. Any potential emboli are trapped within the embolic filter assembly 602 and can be removed along with the catheter 600.

Figure 51:
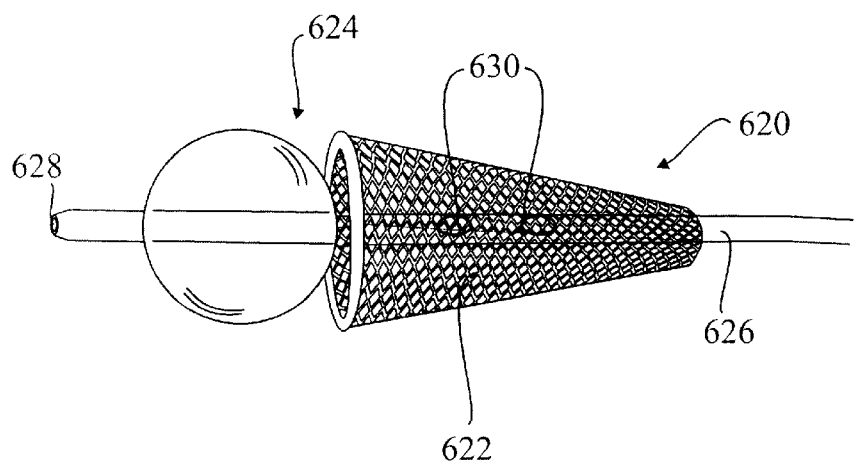
FIG. 51 shows an embodiment of a perfusion filter catheter that combines an embolic filter assembly with an inflatable balloon aortic occlusion device.

FIG. 51 shows an embodiment of a perfusion filter catheter 620 that combines an embolic filter assembly 622 with an inflatable balloon aortic occlusion device 624. The embolic filter assembly 622 may be any one of the actively or passively deployed embolic filter assemblies described herein. Preferably, the inflatable balloon aortic occlusion device 624 is an elastomeric balloon of sufficient inflated diameter to occlude the ascending aorta and is mounted on the elongated catheter shaft 626 upstream of the embolic filter assembly 622. Alternatively, the inflatable balloon aortic occlusion device 624 may be positioned to occlude the inlet end of the embolic filter assembly 622 to minimize the area of contact between the perfusion filter catheter 620 and the aortic wall. The inflatable balloon aortic occlusion device 624 is connected to an inflation lumen within the elongated catheter shaft 626. A cardioplegia lumen, which may also serve as a guidewire lumen, connects to a cardioplegia port 628 at the distal end of the catheter shaft 626. A perfusion lumen connects to one or more perfusion ports 630 located on the catheter shaft 626 downstream from the inflatable balloon aortic occlusion device 624, but upstream of the embolic filter assembly 622. The operation of the perfusion filter catheter 620 of FIG. 51 is quite similar to that described for the embodiment of FIGS. 46–50.

Figure 52:
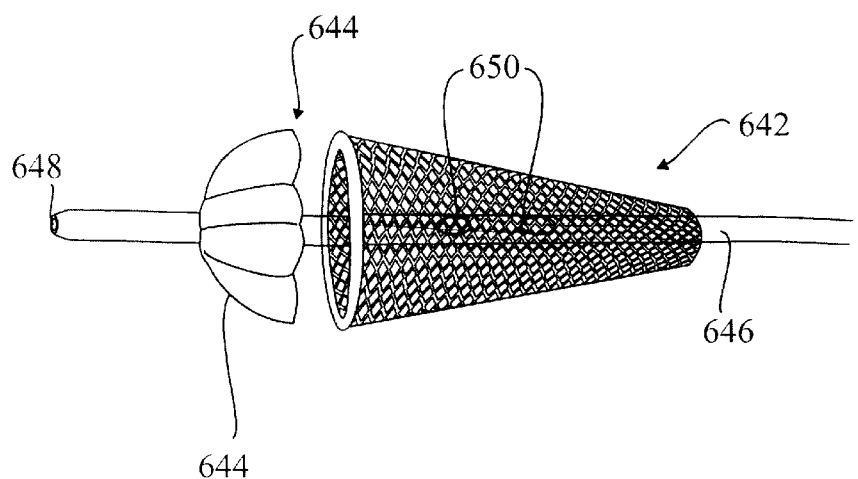
FIG. 52 shows an embodiment of a perfusion filter catheter that combines an embolic filter assembly with a selectively deployable external catheter flow control valve.

FIG. 52 shows an embodiment of a perfusion filter catheter 640 that combines an embolic filter assembly 642 with a selectively deployable external catheter flow control valve 644. The embolic filter assembly 642 may be any one of the actively or passively deployed embolic filter assemblies described herein. The selectively deployable external catheter flow control valve 644 is mounted on the elongated catheter shaft 646 upstream of the embolic filter assembly 642. Alternatively, the selectively deployable external catheter flow control valve 644 may be positioned to occlude the inlet end of the embolic filter assembly 642 to minimize the area of contact between the perfusion filter catheter 640 and the aortic wall. Selectively deployable external catheter flow control valves suitable for this application are described in commonly owned, copending U.S. patent applications Ser. Nos. 08/665,635, 08/664,361 and 08/664,360, filed Jun. 17, 1996, which are hereby incorporated by reference in their entirety. The elongated catheter shaft 646 may include one or more deployment lumens as needed for actuating the external catheter flow control valve 644. A cardioplegia lumen, which may also serve as a guidewire lumen, connects to a cardioplegia port 648 at the distal end of the catheter shaft 646. A perfusion lumen connects to one or more perfusion ports 650 located on the catheter shaft 646 downstream from the external catheter flow control valve 644, but upstream of the embolic filter assembly 622. The operation of the perfusion filter catheter 640 of FIG. 52 is quite similar to that described for the embodiment of FIGS. 46–50.

Figure 53:
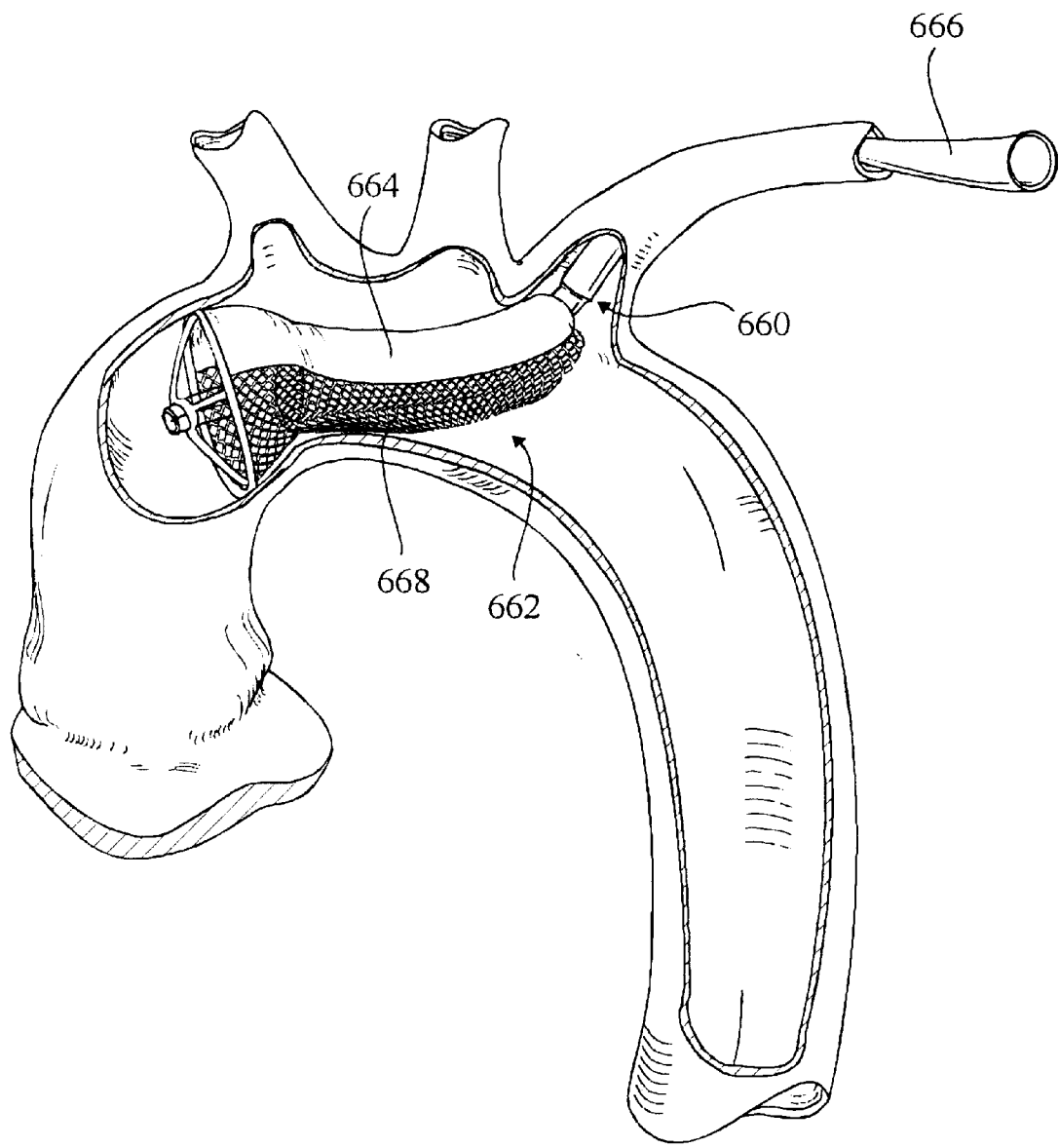
FIG. 53 shows an embodiment of a perfusion filter catheter with an embolic filter assembly having areas of different filter porosity.

FIG. 53 shows an additional feature of the present invention that may be used in combination with many of the features and embodiments previously described. FIG. 53 shows an embodiment of a perfusion filter catheter 660 with an embolic filter assembly 662 having areas of different filter porosity. The embolic filter assembly 662 is mounted on an elongated catheter shaft 666 that may be adapted for peripheral introduction via the femoral artery or subclavian artery or for central insertion directly into the ascending aorta. The embolic filter assembly 662 may resemble any one of the actively or passively deployed embolic filter assemblies described herein. Preferably, the embolic filter assembly 662 assumes one of the surface area increasing geometries described above, such as a trumpet-style embolic filter assembly 662 as shown. The embolic filter assembly 662 is divided along a longitudinal dividing line into areas of different filter porosity. In a preferred embodiment, the embolic filter assembly 662 has an upper portion 664 of finer porosity facing toward the aortic arch vessels and a lower portion 668 of courser porosity facing away from the aortic arch vessels. Preferably, the elongated catheter shaft 666 will have a preformed curve to help orient the upper portion 664 and the lower portion 668 of the embolic filter assembly 662 in the proper position once deployed. The filter mesh of the upper portion 664 may be selected to exclude both macroemboli and microemboli, and the filter mesh of the lower portion 668 may be selected to exclude macroemboli only. Alternatively, the upper portion 664 may be impermeable so as to act like a shunt to direct potential emboli downstream away from the aortic arch vessels.

Figure 54:
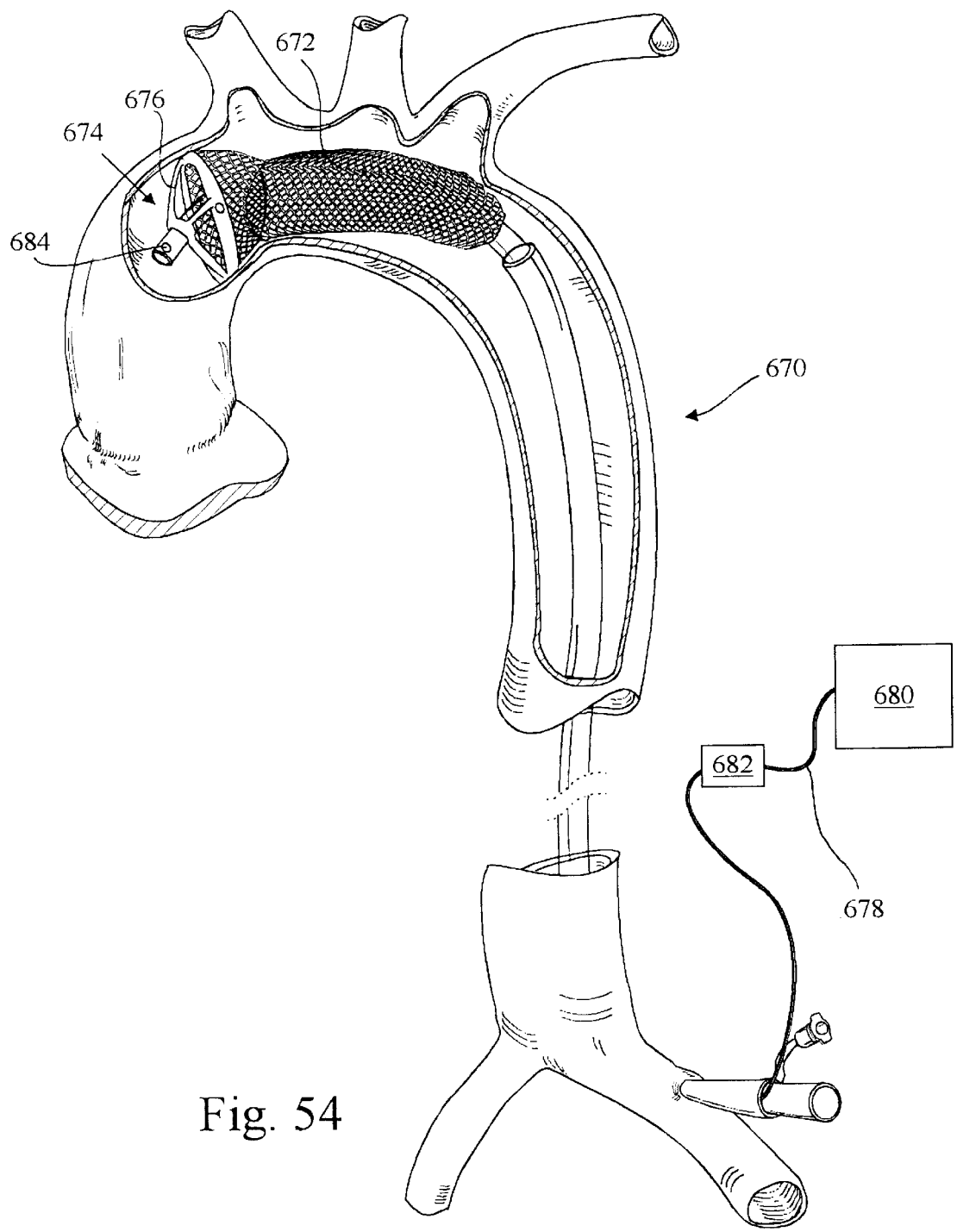
FIG. 54 shows an embodiment of a perfusion filter catheter with a fiberoptic system for aortic transillumination.

Another feature that may be combined with the features and embodiments of the present invention is an aortic transillumination system for locating and monitoring the position of the catheter, the filter and the optional occlusion devices without fluoroscopy by transillumination of the aortic wall. Aortic transillumination systems using optical fibers and/or light emitting diodes or lasers suitable for this application are described in commonly owned, copending U.S. patent application Ser. No. 60/088,652, filed Jun. 9, 1998, which is hereby incorporated by reference in its entirety. By way of example, FIG. 54 shows an embodiment of a perfusion filter catheter 670 with a fiberoptic system for aortic transillumination. A first optical fiber 684 is positioned near a distal end of the perfusion filter catheter 670, upstream of the embolic filter assembly 672, so that it will emit a first laterally directed beam of light. A second optical fiber 672 is positioned on the outer rim of the filter support structure 674 so that it will emit a second laterally directed beam of light. An optical coupling 682 at the proximal end of the perfusion filter catheter 670 connects the optical fibers 684, 672 to a light source 680 by way of an optical cable 678. The light beams emitted by the optical fibers 684, 672 are visible through the aortic wall and can be used to locate and monitor the position and the deployment state of the perfusion filter catheter 670 and the embolic filter assembly 672. Similarly, in embodiments of the perfusion filter catheter utilizing an aortic occlusion device, one or more optical fibers or other light emitting devices may be positioned on the aortic occlusion device to locate and monitor its position and state of deployment.

Likewise, the features and embodiments of the present invention may also be combined with a bumper location device for facilitating catheter insertion and positioning by providing tactile feedback when the catheter device contacts the aortic valve. Bumper location devices suitable for this application are described in commonly owned, copending U.S. patent application Ser. Nos. 60/060,158, filed Sep. 26, 1997, and 60/073,681, filed Feb. 4, 1998, which are hereby incorporated by reference in their entirety.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A perfusion filter catheter comprising:
   an elongated catheter shaft,
   an embolic filter assembly having a porous filter mesh mounted on said catheter shaft, said embolic filter assembly being expandable to engage an inner surface of a patient's aorta, said embolic filter assembly including a plurality of standoff members spaced apart from and surrounding said filter mesh for holding said filter mesh away from an inner wall of the aorta when said embolic filter assembly is in an expanded state.

2. The perfusion filter catheter of claim 1, wherein said embolic filter assembly is configured to expand passively in response to blood flow in the aorta.

3. The perfusion filter catheter of claim 1, wherein said embolic filter assembly is resiliently biased toward the expanded state.

4. The perfusion filter catheter of claim 1, wherein said embolic filter assembly includes a means to actively expand said embolic filter assembly within the aorta.

5. The perfusion filter catheter of claim 4, wherein said means to actively expand said embolic filter assembly comprises a plurality of actuation members connected to an outer periphery of said embolic filter assembly.

6. The perfusion filter catheter of claim 5 wherein said actuation members comprise a plurality of actuation wires slidably received within at least one actuation wire lumen within said elongated catheter shaft, said actuation wires having distal ends connected to the outer periphery of said embolic filter assembly.

7. The perfusion filter catheter of claim 1, wherein said embolic filter assembly has an outer periphery and said elongated catheter shaft is approximately tangential to said outer periphery of said embolic filter assembly when said embolic filter assembly is in the expanded state.

8. The perfusion filter catheter of claim 1 wherein said filter mesh comprises a plurality of regions having different pore sizes.

9. The perfusion filter catheter of claim 1 wherein said standoff members comprise a plurality of longitudinally oriented wire standoff members.

10. The perfusion filter catheter of claim 1 wherein said embolic filter assembly is configured with a conical upstream section and an approximately cylindrical extension extending downstream of said conical upstream section.

11. The perfusion filter catheter of claim 1 further comprising a perfusion lumen within said elongated catheter shaft, said perfusion lumen being fluidly connected to a perfusion port on said elongated catheter shaft upstream of said filter mesh.

12. A perfusion filter catheter comprising:
    an elongated catheter shaft,
    an embolic filter assembly having a porous filter mesh mounted on said catheter shaft, said embolic filter assembly being expandable to engage an inner surface of a patient's aorta, said embolic filter assembly including a cage spaced apart from and surrounding said filter mesh for holding said filter mesh away from an inner wall of the aorta when said embolic filter assembly is in an expanded state.

13. The perfusion filter catheter of claim 12, further comprising a perfusion lumen within said elongated catheter shaft, said perfusion lumen being fluidly connected to a perfusion port on said elongated catheter shaft upstream of said filter mesh.

14. The perfusion filter catheter of claim 12, wherein said embolic filter assembly is configured with a conical upstream section and an approximately cylindrical extension extending downstream of said conical upstream section.

15. The perfusion filter catheter of claim 12, wherein said filter mesh includes a first pore size configured to capture microemboli and a second pore size configured to capture macroemboli.

16. The perfusion filter catheter of claim 15, wherein said first pore size is in the range of 1 to 100 micrometers and said second pore is in the range of 50 to 200 micrometers.

17. A perfusion filter catheter comprising:

an elongated catheter shaft, an embolic filter assembly having a porous filter mesh mounted on said catheter shaft, said embolic filter assembly being expandable to engage an inner surface of a patient's aorta, said embolic filter assembly including a plurality of standoff members for holding said filter mesh away from an inner wall of the aorta when said embolic filter assembly is in an expanded state, said plurality of standoff members forming a generally cylindrical assembly.

18. The perfusion filter catheter of claim 17, wherein said plurality of standoff members comprise a plurality of longitudinally oriented wires.

19. The perfusion filter catheter of claim 17, wherein said plurality of standoff members comprise a plurality of coiled wire standoff members surrounding said filter mesh.

20. The perfusion filter catheter of claim 17, wherein said plurality of standoff members are constructed of a resilient polymer.

21. The perfusion filter catheter of claim 17, wherein said plurality of standoff members arc constructed of an elastic metal alloy.

22. The perfusion filter catheter of claim 17, wherein said plurality of standoff members are constructed of a super-elastic metal alloy.

23. The perfusion filter catheter of claim 17, wherein said plurality of standoff members are constructed of a shape-memory material.

24. A perfusion filter catheter comprising:

an elongated catheter shaft, an embolic filter assembly having a porous filter mesh mounted on said catheter shaft, said embolic filter assembly being expandable to engage an inner surface of a patient's aorta, said embolic filter assembly including a generally cylindrical cage surrounding said filter mesh for holding said filter mesh away from an inner wall of the aorta when said embolic filter assembly is in an expanded state.

25. The perfusion filter catheter of claim 24, wherein said cage comprises a course netting surrounding said filter mesh.

* * * * *